US008097597B2

(12) United States Patent
Schlingensiepen et al.

(10) Patent No.: US 8,097,597 B2
(45) Date of Patent: Jan. 17, 2012

(54) USE OF LOW DOSES OF OLIGONUCLEOTIDES ANTISENSE TO TGF-β GENES IN THE TREATMENT OF BRAIN TUMORS

(75) Inventors: Karl-Hermann Schlingensiepen, Donaustauf (DE); Reimar Schlingensiepen, Regensburg (DE)

(73) Assignee: Antisense Pharma GmbH, Regensburg (DE)

( * ) Notice: Subject to any disclaimer, the term of this patent is extended or adjusted under 35 U.S.C. 154(b) by 321 days.

(21) Appl. No.: 11/792,041

(22) PCT Filed: May 4, 2006

(86) PCT No.: PCT/EP2006/062067
§ 371 (c)(1),
(2), (4) Date: Aug. 5, 2008

(87) PCT Pub. No.: WO2006/117400
PCT Pub. Date: Nov. 9, 2006

(65) Prior Publication Data
US 2009/0306176 A1    Dec. 10, 2009

Related U.S. Application Data

(60) Provisional application No. 60/680,493, filed on May 13, 2005.

(30) Foreign Application Priority Data

May 5, 2005   (EP) ..................................... 05009802

(51) Int. Cl.
*A61K 48/00*   (2006.01)
*C07H 21/04*   (2006.01)
*C07H 21/02*   (2006.01)
(52) U.S. Cl. .......................... 514/44; 536/23.1; 536/24.5
(58) Field of Classification Search ........................ None
See application file for complete search history.

(56) References Cited

FOREIGN PATENT DOCUMENTS

| EP | 1 008 649 | 6/2000 |
|---|---|---|
| EP | 1 877 070 | 12/2008 |
| WO | WO 94/25588 | 11/1994 |
| WO | WO-98/33904 | 8/1998 |
| WO | WO 99/63975 | 12/1999 |
| WO | WO-01/68146 | 9/2001 |

OTHER PUBLICATIONS

Marzo et al. (Cancer Research, 1997, 57, pp. 3200-3207).*
Monia et al. (The Journal of Biological Chemistry, 1996, vol. 271, No. 24, pp. 14533-14540).*
Mahato et al. (Expert Opinion on Drug Delivery, Jan. 2005, vol. 2, No. 1, pp. 3-28).*
Scherer et al. (Nat. Biotechnol., 2003, 21(12), pp. 1457-1465).*
Theodosopoulos, V. P., et al., "Temozolomide in the Treatment of Recurrent Malignant Glioma," Abstract: CNS Tumors (www.asco.org) 2001.
Schlingensiepen, R. et al., "Intracerebral and Intrathecal Infusion of the TGF-β2-Specific Antisense Phosphorothioate Oligonucleotide AP 12009 in Rabbits and Primates: Toxicology and Safety," Oligonucleotides 15:94-104 (2005).
Nielsen, E. P. et al., "Sequence-Selective Recognition of DNA by Strand Displacement with a Thymine-Substituted Polyamide," SCIENCE pp. 1497-1500.
Langer, Robert, "New Methods of Drug Delivery," SCIENCE (Sep. 1990) pp. 1527-1533.
EL-Hariri, M. L et al., "The Mitigating Effects of Phosphatidycholines on Bile Salt-and Lysophosphatidylcholine-induced Membrane Damage," J. Pharm. Pharmacol. 1992:44:651-654.
D'Hellencourt, L. Christian, "Immunomodulation by cytokine antisense oligonucleotides," Eur. Cytokine Netw., vol. 6, Jan.-Feb. 1995, 7-19.
Takahashi, H. et al., "The Use of a Perfluorochemical Emulsion as a Vascular Perfusate in Drug Absorption," J. Pharm. Pharmacol 1998, 40: 252-257.
Yamashita, S. et al., "Effects of diclofenac sodium and disodium ethylenediaminetetraacetate on electrical parameters of the mucosal membrane and their relation to the permeability enhancing effects in the rat jejunum," J. Pharm. Pharmacol 1987, 39:621-626.
Muranishi, Shozo, "Absorption Enhancers," Critical Reviews in Therapeutic Drug Carrier Systems, vol. 7, Issue 1 (1990).
Buur, Anders, "Penetration of 5-Fluorouracil and Prodrugs Across the Intestine of the Albino Rabbit: Evidence for Shift in Absorption Site from the Upper to Lower Region of the Gastrointestinal Tract by Prodrugs," Journal of Controlled Release, 14 (1990) pp. 43-51.
Wang, Qin et al., "Antisense Oligodeoxynucleotides Selectively Suppress Expression of the Mutant α2(I) Collagen Allele in Type IV Osteogenesis Imperfecta Fibroblasts, A Molecular Approach to Therapeutics of Dominant Negative Disorders," The Journal of Clinical Investigation, vol. 97, No. 2, Jan. 1996, 448-454.
Lewis, H. Danny, "Controlled Release of Bioactive Agents from Lactide/Glycolide Polymers," Lactide/Glycolide Polymers, pp. 1-41.
Lee, H.L. Vincent et al., "Mucosal Penetration Enhancers for Facilitation of Peptide and Protein Drug Absorption," Critical Reviews in Therapeutic Drug Carrier Systems, 8(2):91-192 (1991).
Krieg M. Arthur, "CpG Motifs in Bacterial DNA and Their Immune Effects," Annu. Rev. Immunol. 2002 20:709-760.

(Continued)

*Primary Examiner* — Amy Bowman
(74) *Attorney, Agent, or Firm* — Morrison & Foerster LLP

(57) ABSTRACT

This invention is related to the use of at least one oligonucleotide with a length of from about 8 to about 30 nucleotide building blocks for manufacturing a pharmaceutical preparation for the prophylaxis and/or the treatment of diseases, that are modulated by TGF-beta2, TGF-beta1, TGF-beta3, VEGF, interleukin-10, c-jun, c-fos, and/or prostaglandin E2 in a mammal, wherein said oligonucleotide hybridizes with a messenger RNA of a TGF-beta2, TGF-beta1, TGF-beta3, VEGF, interleukin-10, c-jun, c-fos and/or prostaglandin E2 gene and wherein said preparation comprises said oligonucleotide in a concentration of about 1 microM to about 25 microM.

9 Claims, 7 Drawing Sheets

OTHER PUBLICATIONS

Figure 1:
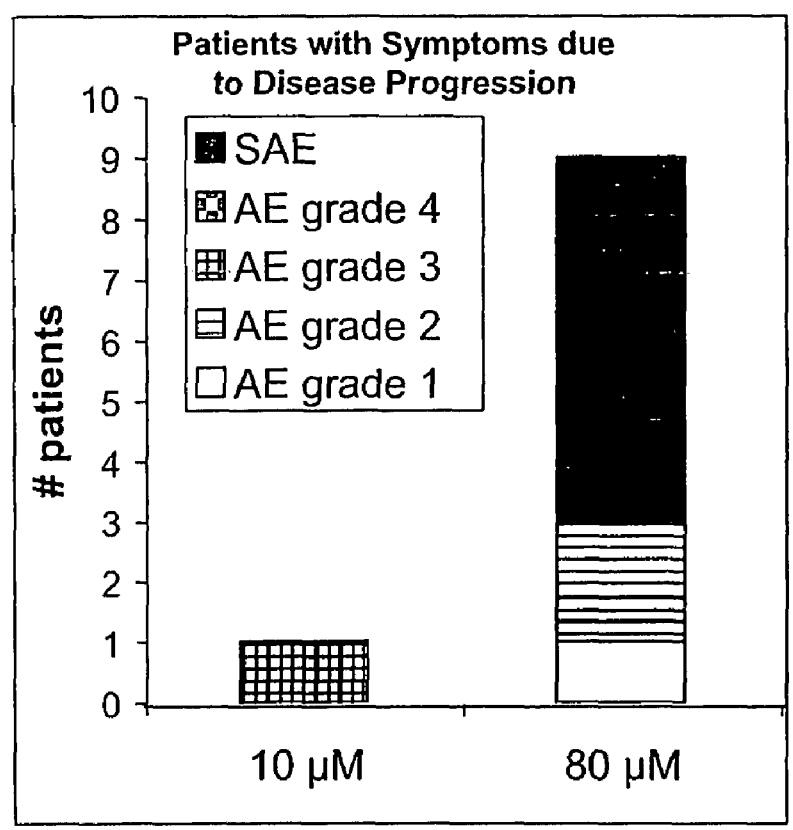
Figure 2A:
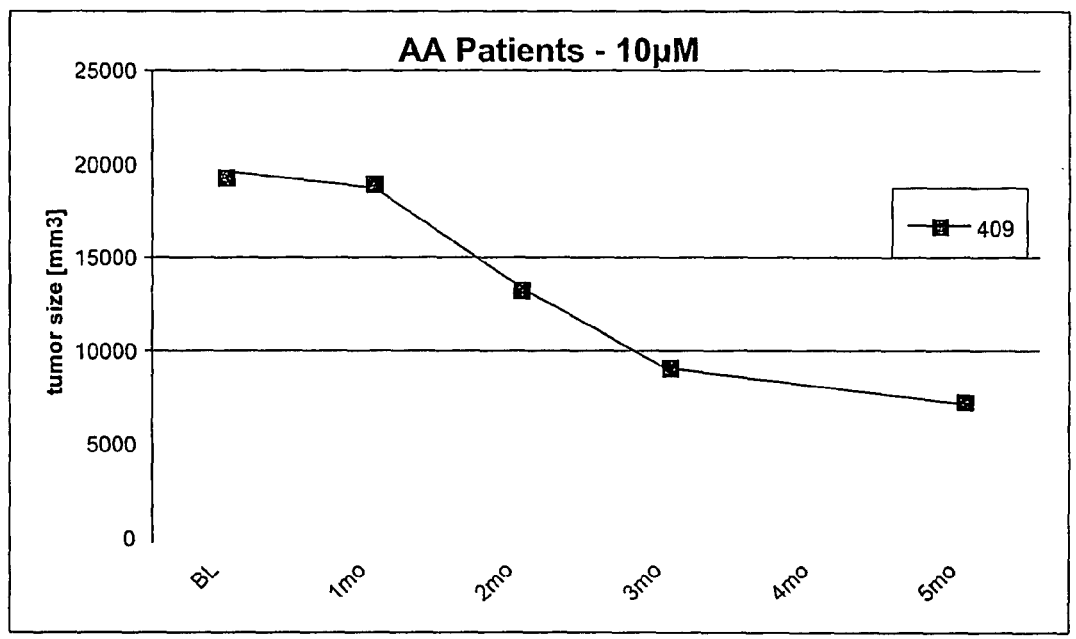
Figure 2B:
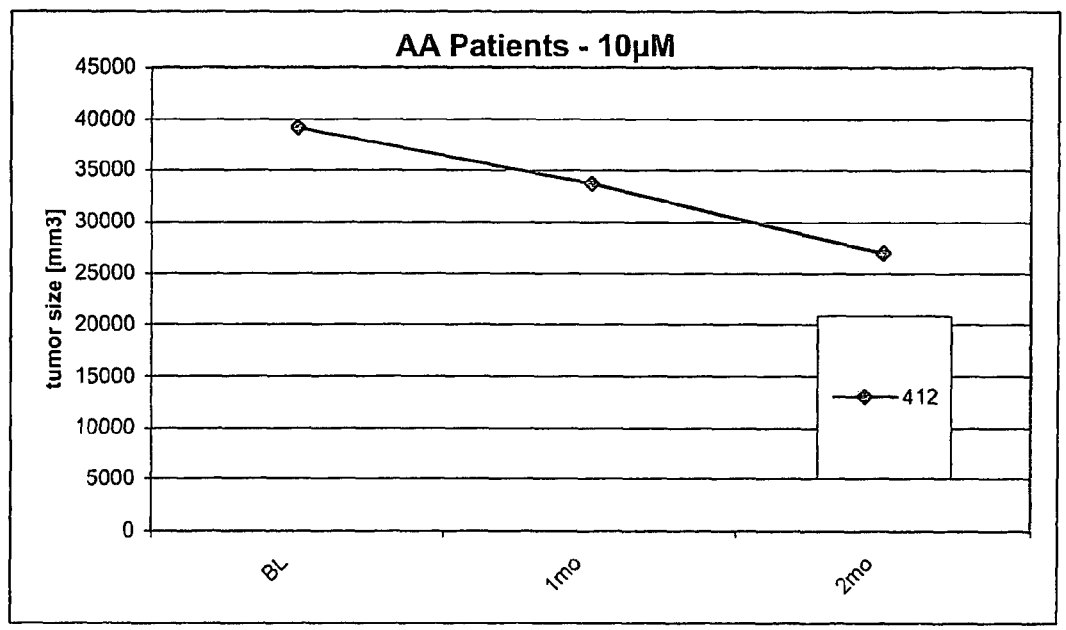
Figure 2C:
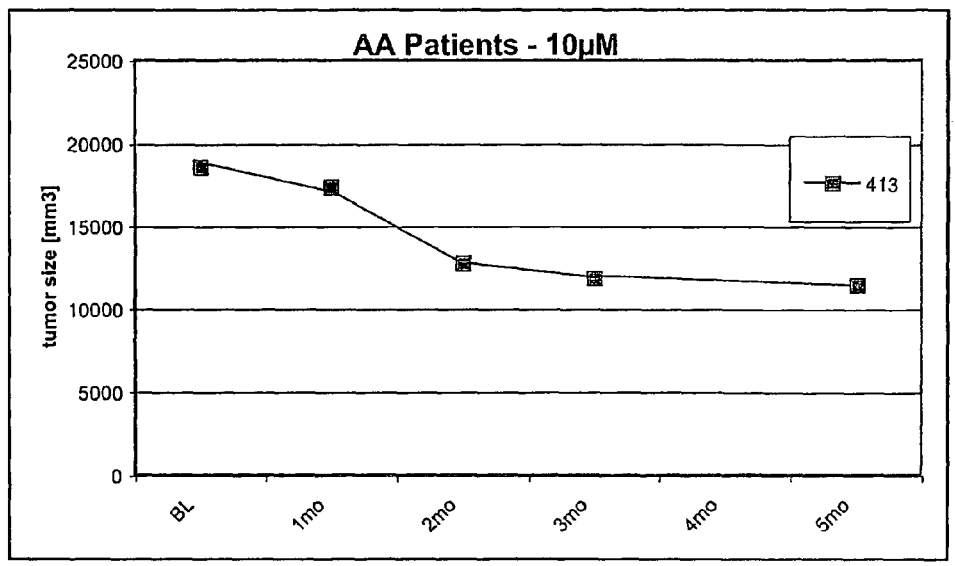
Figure 2D:
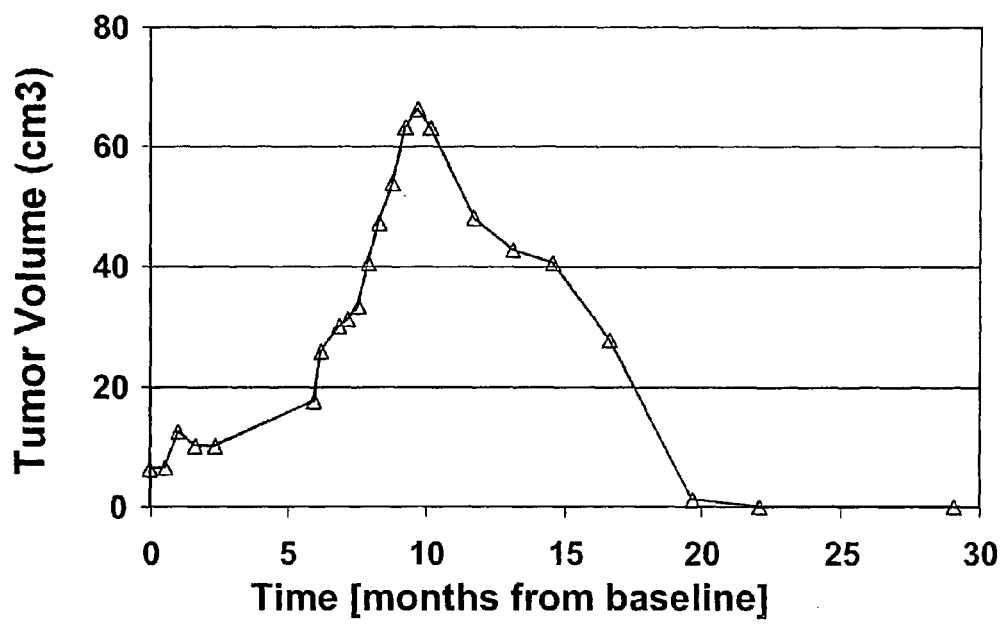

Brunton, "Bile Acids," Section IV Drugs Affecting Gastrointestinal Function, pp. 934-935.

Spearman M et al., "Antisense oligodeoxyribonucleotide inhibition of *TGF*-γ1 gene expression and alterations in the growth and malignant properties of mouse fibrosarcoma cells." Gene, vol. 149, No. 1, Nov. 4, 1994, pp. 25-29.

European Search Report for EP 08173070.7, mailed Jul. 14, 2009, 11 pages.

International Search Report for PCT/EP2006/062067, mailed Nov. 27, 2006, 6 pages.

Marzo et al., "Antisense Oligonucleotides Specific for Transforming Growth Factor β2 Inhibit the Growth of Malignant Mesothelioma Both in Virtro and in Vivo," Cancer Research (1997) 57:3200-3207.

Monia et al., "Nuclease Resistance and Antisense Activity of Modified Oligonucleotides Targeted to Ha-*ras*," The Journal of Biological Chemistry (1996) 271(24):14533-14540.

\* cited by examiner

Figure 2 - part 1

Figure 2 - part 2

Figure 3 - part 1

Sequence listing:

| Seq. Id. No. | Sequences |
|---|---|
| 1 | gtagtacacgatgg |
| 2 | ctgatgtgttgaagaaca |
| 3 | ctctgatgtgttgaag |
| 4 | cgatagtcttgcag |
| 5 | cggcatgtctattttgta |
| 6 | gctttcaccaaattggaagc |
| 7 | ctggcttttgggtt |
| 8 | cagcacacagtagt |
| 9 | tcgagcttccccca |
| 10 | ccccgagcccaagg |
| 11 | cccgacgagccgg |
| 12 | acgcaccaaggcga |
| 13 | cgggttgtcgagccc |
| 14 | cggcagtgcccg |
| 15 | cgcaattctgctcg |
| 16 | ttcgttgtgctccc |
| 17 | attccgactcggtg |
| 18 | acgtgcgtcatcaccgt |
| 19 | ccaagaagcc |
| 20 | cctaatgccttcca |
| 21 | tcagcagggccagg |
| 22 | gcaaagttcagcagggc |
| 23 | ggcaaagttcagcagg |
| 24 | gtggcaaagttcagcagg |
| 25 | gtggcaaagttcag |
| 26 | gaccgtggcaaagttcag |
| 27 | agagaggctgaccgt |
| 28 | gagagagagaggctgac |
| 29 | acagagagaggctga |
| 30 | gtggacagagagagg |
| 31 | caactggacagagagagg |
| 32 | tcttcttgatgtggcc |
| 33 | ccctcttcttcttgatg |
| 34 | caccctcttcttct |
| 35 | atggatttctttggcat |
| 36 | ggatttctttggc |
| 37 | aagttggactctcttctc |
| 38 | taagttggactctcttct |
| 39 | taggagtggttgaggc |
| 40 | gtgtaggagtggttgag |
| 41 | ctgtgtaggagtgg |
| 42 | cccacatgcctgtg |
| 43 | cgatgaacaacgag |
| 44 | ctggcgatgaacaacg |

Figure 3 - part 2

| | |
|---|---|
| 45 | cgctggcgatgaac |
| 46 | gagctagtcccgttg |
| 47 | gcgaagagctagtcc |
| 48 | ccagttatgcgaagagc |
| 49 | ccccagttatgcgaag |
| 50 | cggctcaccgcctcggc |
| 51 | catttgttgtgctgtagg |
| 52 | ggtctgcattcacatttg |
| 53 | catctgcaagtacgttcg |
| 54 | cacatctgcaagtacgtt |
| 55 | gtcacatctgcaagtacg |
| 56 | gcttgaagatgtacctcg |
| 57 | gtaaaactggatcatctc |
| 58 | cttcttttgcaagtctgt |
| 59 | tgagctgtgcatgccttc |
| 60 | agtcaggaggaccag |
| 61 | tgggtgccctggcct |
| 62 | catgttaggcaggtt |
| 63 | aggcatctcggagatct |
| 64 | aaagtcttcactctgc |
| 65 | aacaagttgtccagctg |
| 66 | catcacctcctccag |
| 67 | gggtcttcaggttctccc |
| 68 | cacggccttgctcttgtt |
| 69 | ttattaaaggcattcttc |
| 70 | aagatgtcaaactcactc |
| 71 | gtagttgatgaagatgtc |
| 72 | gattttggagacctct |
| 73 | tcagctatcccagagc |
| 74 | ggctgggtcagctat |
| 75 | aaatcgttcacagagaag |
| 76 | tctttctaaatcgttcac |
| 78 | cagttcggactatact |
| 79 | gcccaagttcaaca |
| 80 | catagaaggtcgtttc |
| 81 | aggtttgcgtagac |
| 82 | gttcctcatgcgcttc |
| 83 | gtttgcaactgctg |
| 85 | gtccgtgcagaagtcctg |
| 86 | ggaagaaactatgagagt |
| 87 | cttagggaagaaactatg |
| 88 | agaacaaagaagagcc |
| 89 | cagcaagagaacaaag |
| 90 | cgacattcagtaaaagtg |
| 91 | cttctggagataactaga |
| 92 | cataagacacagtcttac |
| 93 | gaaagcataagacacagt |

USE OF LOW DOSES OF OLIGONUCLEOTIDES ANTISENSE TO TGF-β GENES IN THE TREATMENT OF BRAIN TUMORS

This is a 371 of PCT/EP06/062067 filed May 4, 2006, claiming benefit of U.S. provisional application No. 60/680,493, filed May 13, 2005.

FIELD OF INVENTION

The present invention is directed towards the preparation of a pharmaceutical composition for the prophylaxis and/or treatment of diseases that are modulated by TGF-beta1, TGF-beta2, TGF-beta3, VEGF, interleukin-10, c-jun, c-fos and/or prostaglandin E2 gene.

INTRODUCTION

An overall feature of pharmaceutical substances is their increasing efficacy accompanied by an increase in amounts being administered. Particular substances used in tumor therapy show a strong correlation between the total amount administered and the inhibition of tumor growth. Additionally, cellular uptake is a limiting factor for the efficacy of "in vivo" administration of oligonucleotides, where conventionally high concentrations and high amounts of oligonucleotides are administered to inhibit the production of the respective protein.

Nevertheless, the clinical success of these substances is limited since an increase in the concentration and the total amount of these substances, which can be administered to a mammal suffering from tumor metastases, nerval disease and immunosuppression, is correlated with a strong increase in severe side effects and toxicity.

Up till now for the therapy of cancer, metastases, disease of the nervous system and immunosuppression there are no results of clinical trials giving evidence of the amount of oligonucleotides that are successful in tumor therapy.

EP 1008 649 and EP 0695354 teach that oligonucleotides hybridizing with the mRNA of TGF-beta 1 and/or TGF-beta 2 can be used for manufacturing pharmaceutical compositions. EP 1 089 764 further teaches that inhibitors of substances negatively effecting the immune system in combination with oligonucleotides hybridizing with the mRNA of TGF-beta, VEGF, interleukin 10, and prostaglandin E2 and their respective receptors can be used for manufacturing a pharmaceutical composition as well. But these patents offer a wide range of concentrations in which the oligonucleotides can be administered.

The results of toxicological studies in mammals showed that it is possible to administer high amounts of oligonucleotides to inhibit the production of the respective targets without toxicological side effects (see Examples 1, 2, 3 and Schlingensiepen, R. et al, 2005). Consequently, it would have been obvious to administer high concentrations and high amounts of oligonucleotides to inhibit the targets involved in the therapy of cancer, metastases, disease of the nervous system and immunosuppression.

SUMMARY OF THE INVENTION

Surprisingly, we recognized during clinical trials, that pharmaceutical compositions containing at least one oligonucleotide in lower concentration and/or administered with lower daily amounts inhibit tumor growth faster and with less symptoms during disease progression than the higher concentrations and/or higher daily amounts.

Figure 4:
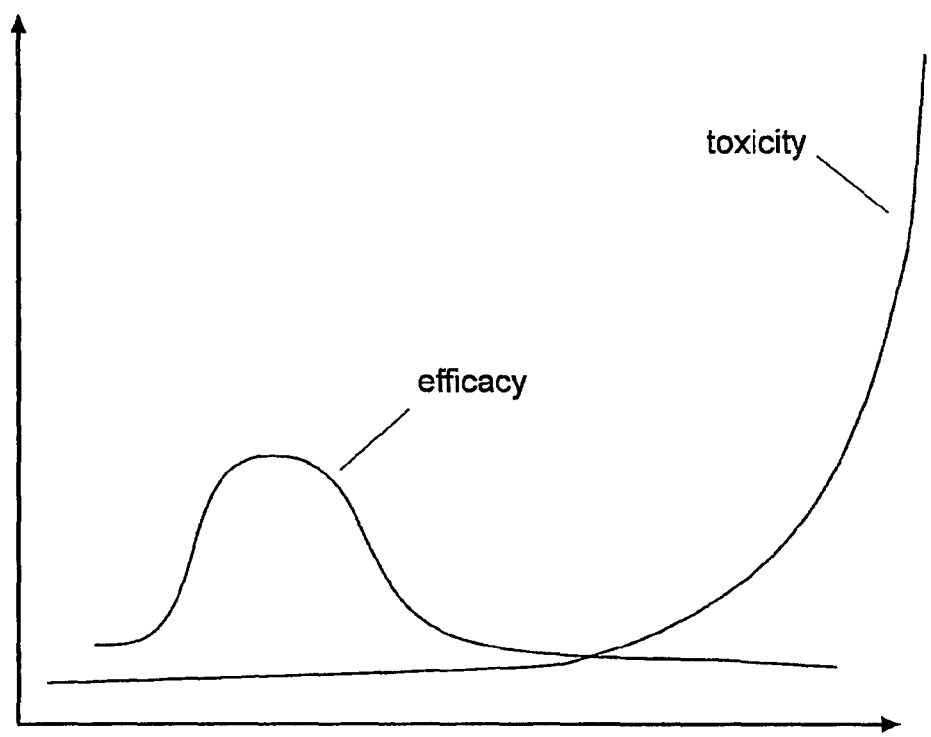

Additionally these concentrations or daily amounts were 10 to 50 fold lower than the maximal concentration tested in toxicological studies without severe side effects (see also FIG. 4).

That at least one oligonucleotide used for manufacturing a pharmaceutical preparation of this invention has a concentration of about 1 microM to about 25 microM and a length of about 8 to about 30 nucleotide building blocks, is administered for the prophylaxis and/or treatment of diseases that are modulated by TGF-beta1, TGF-beta2, TGF-beta3, VEGF, interleukin-10, c-jun, c-fos and/or prostaglandin E2 and hybridizes with the messenger RNA of a TGF-beta1, TGF-beta2, TGF-beta3, VEGF, interleukin-10, c-jun, c-fos, and/or prostaglandin E2 gene.

A further aspect of this invention is the administration of said pharmaceutical preparation by infusion to a tissue, a body cavity or a tumor at a flow rate of about 0.1 microL/min to about 2 mL/min or by bolus injection.

Yet another aspect of this invention is the application of the at least one oligonucleotide to a tissue, a tumor, a body cavity in amounts of about 0.15 nmol to about 3 micromol, when administered to a tumor, a tissue or a body cavity selected from the group of joint cavity or ventricular space, respectively in amounts of about 0.005 micromol to about 0.06 mmol, when administered to a large body cavity, such as intraperitoneal space or the pleural space in amounts of bout 0.005 micromol to about 0.05 mmol Further advantages of the embodiments of modifications described in this invention are enhanced efficacy, enhanced affinity for nucleic acid target, enhanced cellular uptake, enhanced safety, less side effects, and increased stability in the presence of nucleases.

FIGURES

FIG. 1 shows the number of anaplastic astrocytoma patients with symptoms due to the disease progression after treatment with 10 microM and 80 microM solutions (0.9% sodium chloride) of the oligonucleotide hybridized with the mRNA of TGF-beta2, identified in the sequence listing with SEQ ID NO 5, administered intratumorally by convection enhanced delivery CED at a flow rate of 4 microL/min. As can be seen in FIG. 1, the number of anaplastic astrocytoma patients with symptoms due to tumor progression, as well as the grade and severity of these effects after treatment with the 10 MicroM solution of said oligonucleotide reduced compared to patients infused with the 80 microM solution of said oligonucleotide. See more details in Example 3. Grades were defined according to the NCI CTC Toxicity Scale Version 2.0. The SAEs (=serious adverse events) were defined as any untoward medical occurrence as a result of such dose, which e.g. results in life-threatening effects, requires patient hospitalization, or prolongation of existing hospitalization.

FIG. 2 shows the reduction of tumor size over a couple of months in four anaplastic astrocytoma patients treated with a 10 microM (FIG. 2A, 2B, 2C) and 80 microM (FIG. 2D) solution (0.9% sodium chloride, DAB7) of the antisense oligonucleotide against mRNA of TGF-beta2, identified in the sequence listing with SEQ ID NO 5, administered intratumorally by convection enhanced delivery. For more details see Example 10. The three patients treated with 10 microM solution (FIG. 2A, 2B, 2C) a reduction of tumor size over a period of about 2 to 5 months was observed in the range of about 30% to about 66%, whereas the patient treated with 80 microM showed an increase in tumor growth (FIG. 2D). For more details see example 10.

FIG. 3 depicts preferred oligonucleotides, able to hybridize with the mRNA of targets such as TGF-beta1 (SEQ ID NO 1 to 4), TGF-beta2 (SEQ ID NO 5 to 8), TGF-beta3 (SEQ ID NO 9 to 38), prostaglandin E2 (SEQ ID $NO_{39}$ to 49), VEGF (SEQ ID NO 50 to 56), interleukin 10 (SEQ ID NO 57 to 76), c-jun (SEQ ID NO 78 to 83) and c-fos (SEQ ID NO 85 to 93).

FIG. 4 depicts qualitatively the efficacy and toxicity of oligonucleotides correlated with the concentration. The vertical axis qualitatively shows toxicity and efficacy and the horizontal axis shows the concentration of the oligonucleotide. It can be seen in the figure, that a peak of efficacy is reached at a much lower concentration than concentrations showing toxic effects.

Figure 5:
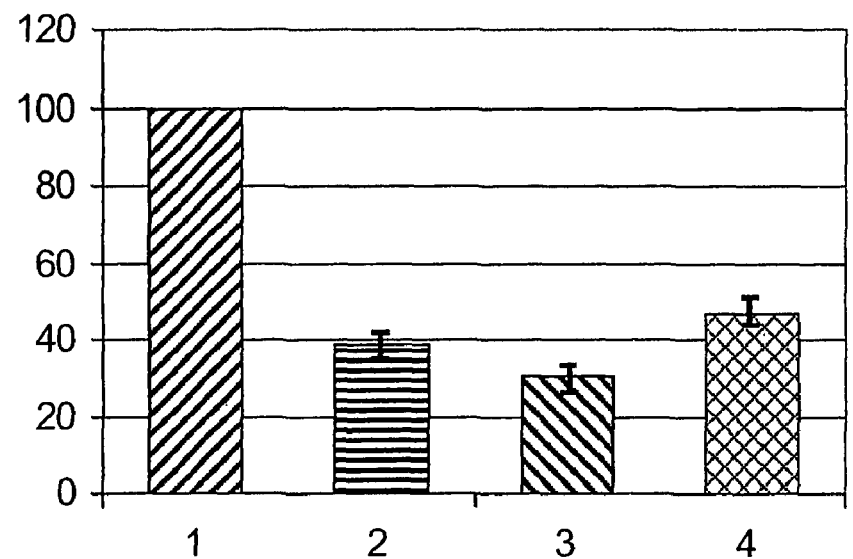

FIG. 5 represents the inhibition of TGF-beta2 secretion by A-172 cells treated with 5 microM, 10 microM, and 80 microM of the oligonucleotide identified with SEQ ID NO 5 over 7 days, shown in percentage of untreated control (bar 1). Incubation of A-172 cells with three different concentrations of this oligonucleotide resulted in a median of inhibition by 61.1% (5 microM, bar 2), 68.1% (10 microM, bar 3), and 56.2% (80 microM, bar 4). Conclusively, 10 microM of the oligonucleotide identified by SEQ ID NO 5 was found to be the best inhibitor of TGF-beta2 expression compared to 5 and 80 microM of this oligonucleotide. Secreted TGF-☐eta2 was quantified by ELISA. Results are taken from four independent experiments. For more details see Example 12.

Figure 6:
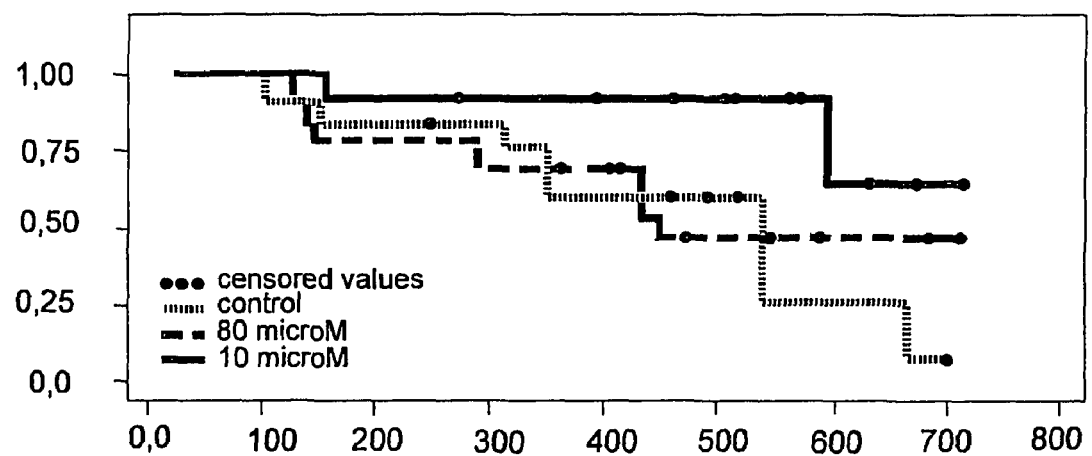

FIG. 6 shows the ratio of patients survived versus time for three treatment groups. In one group SEQ ID NO 5 was administered in a concentration of 10 microM (straight line) and 80 microM (dashed line). Patients of the control group (dotted line) on the other hand received standard chemotherapy. For more details see example 11. Patients who were still alive at time of evaluation, are shown as "censored" values with their respective survival time until evaluation (dots in the curves). This kind of presentation is known as "Kaplan-Meier Survival Curve". The data show that patients treated with 10 microM of SEQ ID NO 5 have a much better chance of survival than those treated with 80 microM and those of the control group.

DETAILED DESCRIPTION OF THE INVENTION

The expression about in the context of this invention comprises deviations from the absolute value given in the text from 0 to 100%, more preferred from 1 to 80%, even more preferred from 2 to 60%, more preferred from 3 to 40%, more preferred from 4 to 20%, and even more preferred from 5 to 10% of the respective value.

Adverse event in the context of this invention is understood as any untoward medical occurrence in a patient or clinical investigation subject after the administration of a pharmaceutical preparation that does not have a causal relationship with the treatment of the respective pharmaceutical preparation. An adverse event can therefore be any unfavourable and unintended sign (including an abnormal laboratory finding), symptom, or disease e.g. due to disease progression. Another expression for adverse event is symptom.

Brain tumor used synonymously with tumor of the brain according to this invention is any tumor of the brain including metastases, metastases derived from other parts of the brain or derived from any other tumor in the body, and metastases of the medulla spinalis. Brain tumor further comprises primary brain tumor, astrocytoma, including glioblastoma and oligoastrocytoma, oligodendroglioma and gliosarcoma.

Cavity in the context of this invention implies, for example, colon, duodenum, ileum, jejunum, joint cavity, pleural cavity, intraperitoneal space, lumen of the oesophagus, larynx, maxilliary sinus, nasal cavity, pharynx, the rectum, the stomach, the intestinal tract, the urinary duct, the urinary bladder, and the ventricular space.

In the present invention the expression disease comprises neoplasms, metastases, neuronal injuries, and immunosuppression.

Hybridizing in the context of this invention implies, that two nucleotide chains at least partly form a double strand by hydrogen bonding. The double strand develops completely when the two nucleotide chains have exact antisense sequences. But even if any nucleotide of an oligonucleotide, also referred to as nucleotide building block is substituted by another nucleotide, the respective nucleotide is modified or even when a spacer is in the place of the respective oligonucleotide, the oligonucleotide can still hybridize with the target molecule, generally the mRNA of a protein, and with this inhibit the production of said protein.

Metastasis in the context of this invention means that at least one cell separates or dissociates from a tumor tissue and moves via e.g. the lymphatic system, the blood vessels, and/or invading the surrounding tissue to another part of the body of a mammal, preferably a human, where it settles down and forms new tumor tissue.

The term oligonucleotides of the invention encompasses any pharmaceutically acceptable salts, esters, or any other compound that upon administration to a mammal is capable of providing the biologically active metabolite or residue thereof. This is accomplished by specific hybridization of the compounds with one or more nucleic acids encoding TGF-beta1, TGF-beta2, TGF-beta3, VEGF, and interleukin-10 and/or prostaglandin E2.

The terms nucleic acids and oligonucleotides are used synonymously in the context of this invention.

In some embodiments, the nucleic acids are not antisense nucleic acids, meaning that they do not function by binding partly or completely to complementary genomic DNA or RNA species within a cell and thereby inhibiting the function of said genomic DNA or RNA species.

In one embodiment the oligonucleotides of this invention also comprise the oligonucleotides as described in the patents EP 069 53 54 and EP 1008649 as well as those of the international patent applications published under No. WO 01/68 146, WO 98/33904, WO 99/63975 and WO 99/63975 herein incorporated by reference. Oligonucleotides hybridizing with TGF-beta in one preferred embodiment include at least one sequence set forth as SEQ ID NOs: 1 to 93.

Oligonucleotides or nucleic acids include oligonucleotides having non-naturally occurring portions with similar function. Naturally occurring nucleotides as well as non-naturally occurring nucleotides, modifications and spacers are also referred to as nucleotide building block. The most common nucleotide building block is a nucleotide. Modified or substituted nucleotides as well as spacers are also comprised by the expression nucleotide building block.

These modified or substituted oligonucleotides are often preferred over native forms because of desirable properties such as enhanced cellular uptake, enhanced affinity for nucleic acid target (e.g. protein), altered intracellular localization and increased stability in the presence of nucleases. Modifications of the oligonucleotides as used herein comprise any chemical modification of the sugar, the base moiety and/or the internucleoside linkage.

In one embodiment, the ring structure of the ribose group of the nucleotides in the modified oligonucleotide or polynucleotide has oxygen in the ring structure substituted with N—H, N—R (with R being an alkyl, more preferred alkyl with 1 to 20 carbons, very preferred alkyls are methyl, ethyl, propyl, isopropyl, butyl, isobutyl, or R is an aryl substituent), S and/or methylene.

Pharmaceutical preparation in the context of this invention comprises an oligonucleotide of this invention within a pharmaceutically acceptable carrier.

In one embodiment nucleic acids or oligonucleotides with a covalently modified base and/or sugar include for example nucleic acids having backbone sugars which are covalently attached to low molecular weight organic groups other than a hydroxyl group at the 3' and/or 2' position or a phosphate group at the 5' position. Thus modified nucleic acids may additionally include at least one 2'-O-substituted ribose group. For purposes of this invention, the term "2'-substituted" means substitution of the 2'-OH of the ribose molecule. The O may be substituted with N, S and the substituent can further comprise an alkyl with 1 to 20 carbons e.g. O-alkyl, S-alkyl, NH-alkyl, N-dialkyl, O-aryl, S-aryl, NH-aryl, O-aralkyl, S-aralkyl, NH-aralky. Preferred embodiments of 2'-O-alkyl-groups are methoxy-, ethoxy-, propyloxy-, isopropyloxy-, methoxy-ethoxy. Further modifications of nucleotide building blocks are also given by U.S. Pat. No. 6,143,881, U.S. Pat. No. 5,591,721, U.S. Pat. No. 5,652,355, U.S. Pat. No. 5,962,425, U.S. Pat. No. 5,969,116 and U.S. Pat. No. 5,914,396 herein incorporated by reference. Another preferred embodiment is a nucleotide building block, comprising at least one deoxyribose, with an alkyl-group bound to the 2'-carbon. The alkyl may have about 1 to about 30 carbons, 1 to about 20 carbons, 1 to about 10 carbons, or 1 to about 5 carbons. Preferred alkyl-groups are ethyl-, propyl-, isopropyl-, butyl-group, highly preferred is the methyl-group.

In yet another embodiment, modified nucleic acids include sugars such as arabinose instead of ribose. Thus the nucleic acids may be heterogeneous in backbone composition thereby containing any possible combination of polymer units linked together such as peptide-nucleic acids (which have amino acid backbone linked to nucleic acid bases). In some embodiments the nucleic acids are homogeneous in backbone composition.

The substituted purines and pyrimidines of the nucleic acids include standard purines and pyrimidines such as cytosine as well as base analogs such as substituted bases (Wagner et al. 1993). Purines and pyrimidines include, but are not limited to adenine, cytosine, guanine, thymine, inosin, 5-methylcytosine, 2-aminopurine, 2-amino-6-chloropurine, 2,6-diaminopurine, hypoxanthine, and other naturally and non-naturally occurring nucleobases, substituted and unsubstituted aromatic moieties.

The single nucleotides in each oligonucleotide may contain the same modifications, may contain combinations of these modifications, or may combine these modifications with phosphodiester linkages. Methods of rendering oligonucleotide nuclease resistant include, but are not limited to, covalently modifying the purine or pyrimidine bases. For example, bases may be methylated, hydroxymethylated, or otherwise substituted (e.g., glycosylated) such that the oligonucleotides or polynucleotides are rendered substantially acid and nuclease resistant.

In a preferred embodiment, at least one end of the oligonucleotide is a biotin, biotin analog, avidin, or avidin analog. These molecules have the ability to block the degradation of the protected oligonucleotide and provide means for high affinity attachment of the modified nucleic acids to the solid support. Avidin and biotin derivatives, which can be used to prepare the reagents of this invention include streptavidin, succinylated avidin, monomeric avidin, biocytin (biotin-epsilon-N-lysine), biocytin hydrazide, amine or sulfhydryl derivatives of 2-iminobiotin and biotinyl-epsilon-aminocaproic acid hydrazide. Additional biotin derivatives, such as biotin-N-hydroxysuccinimide ester, biotinyl-epsilon-aminocaproic acid-N-hydroxysuccinimide ester, sulfosuccinimidyl 6-(biotin amido)hexanoate, N-hydroxysuccinimideiminobiotin, biotinbromoacetylhydrazide, p-diazobenzoyl biocytin and 3-(N-maleimidopropionyl)biocytin, can also be used as end-blocking groups on the oligonucleotides of the present invention.

In yet another embodiment, the base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are bound directly or indirectly to aza nitrogen atoms of the amide portion of the backbone. Representative United States patents that teach the preparation of PNA compounds include, but are not limited to, U.S. Pat. Nos. 5,539,082, 5,714,331, and 5,719,262, each of which is herein incorporated by reference. Further teaching of PNA compounds can be found in Nielsen et al. 1991.

Further backbone modified oligonucleotide includes, for example, phosphorothioates, chiral phosphorothioates, phosphorodithioates, phosphorotriesters, aminoalkylphosphorotriesters, methyl- and other alky-phosphonates including 3'-alkylene phosphonates and chiral phosphonates, phosphinates, phosphoramidates, including 3'-aminophosphoramidate and aminoalkylphosphoramidates, thiono-phosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts, and free acid forms are also included. One preferred embodiment is the sodium salt of the nucleic acid.

In some embodiments at least one nucleotide of an oligonucleotide is modified as described in one of the modifications above. The modification can either cover the oligonucleotide continuously or irregularly.

In yet another embodiment, at least two modifications as described above are combined within one oligonucleotide.

In another embodiment, 1 to about 12 or 1 to about 8 or 1 to about 4 or 1 to about 2 oligonucleotides and/or nucleotide linkages at the 3' and/or 5' end of the oligonucleotide are modified as described above.

In one embodiment the oligonucleotides of this invention hybridize with a target, e.g. TGF-beta or its subtypes more preferred TGF-beta 1, TGF-beta 2, TGF-beta 3, VEGF, IL-10, and low $PGE_2$. These targets are well known to someone skilled in the art. The antisense structure of the mRNA of said targets is also given in the PCT/EP2004/053604, herein incorporated by reference.

Chain elongation means that oligonucleotides of the sequence listing and other oligonucleotides, that have additional nucleotides of the sequence of the respective antisense structure of the mRNA of said targets, are still within the scope of this invention. The additional nucleotides in one embodiment are according to the coding region of the mRNA, in yet another embodiment, the additional nucleotides are also from the non-coding part of the mRNA, including introns and exons. The additional nucleotides comprise about 1 to about 10,000 nucleotides, about 1 to about 5,000 nucleotides, about 1 to about 3,000 nucleotides, about 1 to about 1,000 nucleotides, about 1 to about 500 nucleotides, about 1 to about 100 nucleotides, about 1 to about 50 nucleotides, about 1 to about 25 nucleotides, about 1 to about 10 nucleotides, about 1 to about 5 nucleotides or about 1 to about 2 nucleotides bound to at least one of the 3' and/or 5' end, in another embodiment, to at least one of the 2' or 5' end. In yet another embodiment, some nucleotide building blocks of these oligonucleotides or polynucleotides may be modified or substituted by spacers and/or modifications as described herein.

Pharmaceutically acceptable salts refer to physiologically and pharmaceutically acceptable salts of the compounds used in the invention, which means that the salts retain the biological activities of the parent compounds without undesired toxicological effects.

In one embodiment the oligonucleotide or its active derivative is a single stranded oligonucleotide, in yet another embodiment the oligonucleotide is double stranded, which means that the oligonucleotide is hybridized completely or partly with a second oligonucleotide that has about 50% to about 100% of the exact antisense structure of said oligonucleotide. This may result in a double strand in which both oligonucleotides hybridize with less bond strength or in double strand with overlapping ends. The two oligonucleotides might have the same length, in other words they have the same amount of nucleotide building blocks or their length might differ, also resulting in overlapping ends on one or both ends.

The expression spacer in the context of this invention comprises any nucleotide building block which is not obviously a derivative or a modification of a nucleotide, but connects two nucleotide building blocks in a way, that the resulting oligonucleotide still hybridizes with its target, e.g. mRNA of TGF-beta1, TGF-beta2, TGF-beta3, VEGF, prostaglandin E2, c-fos, c-jun or interleukin-10.

One embodiment of the invention is the use of at least one oligonucleotide with a length of 8 to 30 nucleotide building blocks for manufacturing a pharmaceutical preparation for the prophylaxis and/or the treatment of diseases that are modulated by TGF-beta1, TGF-beta2, TGF-beta3, VEGF, interleukin-10, c-jun, c-fos, and/or prostaglandin E2 in a mammal, wherein said oligonucleotide hybridizes with a messenger RNA of a TGF-beta1, TGF-beta2, TGF-beta3, VEGF, interleukin-10, c-jun, c-fos and/or prostaglandin E2 gene and wherein said preparation comprises said oligonucleotide in a concentration of about 1 microM to about 25 microM.

In other embodiments the pharmaceutical preparation of this invention comprises oligonucleotides in a concentration of about 1 microM to about 15 microM, more preferred of about 2.5 microM to about 14 microM, more preferred of about 4 microM to about 13 microM, more preferred of about 5 microM to about 12.5 microM, most preferred the concentration of the oligonucleotides is about 20 microM, about 10 microM or about 5 microM.

In yet another embodiment the pharmaceutical preparation of this invention comprises oligonucleotides in a concentration of about 50 microM to about 150 microM, more preferred in concentrations of about 60 microM to about 100 microM, even more preferred of about 70 microM to about 90 microM and most preferred about 80 microM, 60 microM or 100 microM.

Whereas the oligonucleotides of this invention are single stranded, in some embodiments at least parts of the single-stranded nucleic acid are double-stranded. Double-stranded molecules are more stable in vivo, while single-stranded molecules have increased activity.

In one embodiment the oligonucleotide has a length between about 6 to about 30 nucleotides and is complementary to the mRNA of the targets TGF-beta1, TGF-beta2, TGF-beta3, VEGF, interleukin 10, c-jun, c-fos, and prostaglandin E2. In more preferred embodiments the oligonucleotides of this invention have lengths of about 7 to about 25 nucleotides, of about 8 to about 20 nucleotides, even more preferred of about 12 to 18 nucleotides. Preferred embodiments of oligonucleotides usable in this invention are shown in the sequence listing under SEQ ID NOs 1 to 93, very preferred embodiments are SEQ ID NOs 1 to 38, most preferred are SEQ ID NOs 2 and/or 5.

Other oligonucleotides usable in pharmaceutical preparations according to this invention are oligonucleotides described in the sequence listing respectively the examples of EP 1 089 764, EP 0 695 534, PCT/EP98/00497 and PCT/EP2005/002101 herein incorporated by reference.

In other embodiments the at least one oligonucleotide for the manufacturing of a pharmaceutical preparation comprises at least one phosphorothioate linkage between two nucleotide building blocks. The phosphorothioate linkage may cover 0%-5%, 5% to 10%, 10% to 15%, 15% to 20%, 20% to 25%, 25% to 30%, 30% to 35%, 35% to 40%, 40% to 45%, 45% to 50%, 50% to 55%, 55% to 60%, 60% to 65%, 65% to 70%, 70% to 75%, 75% to 80%, 80% to 85%, 85% to 90%, 90% to 95% or 95% to 100% of the linkages. The phosphorothiate linkages may be scattered regularity or irregularity over the oligonucleotide. In some embodiments the phosphorothioate is accumulated at either one or both of the 3' and/or 5' ends of the oligonucleotide. Another preferred embodiment is an oligonucleotide where all linkage between the nucleotides are phosphorothioates.

In one embodiment the oligonucleotide is a single strand oligonucleotide. Single strand means, that all oligonucleotide building blocks are in one line and do not hybridize with a second oligonucleotide or antisense oligonucleotide and are not bound otherwise.

In yet other embodiments the oligonucleotides of this invention are used for the prophylaxis and/or the treatment of a disease selected from the group of cancer, metastases, disease of the nervous system, and immunosuppression.

In other embodiments pharmaceutical preparations of the oligonucleotides are administered by infusion into a tissue, a tumor or a body cavity. In more preferred embodiments the tissue is selected from the group of bile duct, bladder, bone, bone marrow, brain, breast, colon, endometrium, epithelium, gall bladder, head, head and neck, heart, intestine, joints, kidney, larynx, liver, lung, lymphatic node, lymphatic vessels, muscle, oesophagus, ovary, pancreas, prostate, rectum, urinary duct, skin and its layers, spleen, stomach, testis, thymus, thyroid, tonsil, or uterus and/or is administered to the respective tumor of this tissue.

In a more preferred embodiment the pharmaceutical preparation is administered to the tumor in the brain, preferably the brain tumor is selected from the group of astrocytoma including glioblastoma and oligoastrocytoma.

In another embodiment the pharmaceutical preparation of oligonucleotides is administered into a body cavity, selected from the group of bile duct, bladder, colon, gall bladder, joint cavity, pleural cavity, intraperitoneal space, the rectum, the intestinal tract, the urinary duct, the urinary bladder, and the ventricular space.

In yet other embodiments of this invention the pharmaceutical preparations comprising at least one oligonucleotide of this invention are administered to a tumor or a tissue, the joint cavity or the ventricular space with a flow rate of about 0.1 microL/min to about 0.1 mL/min. Further preferred are flows of about 0.5 microL/min to about 0.05 mL/min, more preferred of about 0.8 microL/min to about 0.04 mL/min, more preferred of about 1 microL/min to about 0.02 mL/min, more preferred of about 2 microL/min to about 10 microL/min, most preferred are about 4 microL/min. In a very preferred embodiment the pharmaceutical preparation is administered at these flow rates into a tumor of the brain, more preferred into astrocytoma, including glioblastoma and oligoastrocytoma.

In another embodiment the pharmaceutical preparation is administered into body cavities that are not the ventricular space or joint cavity, eg. colon, pleural cavity, intraperitoneal space, the rectum, the stomach, the intestinal tract, the urinary duct, or the urinary bladder. In these embodiments the pharmaceutical preparation is administered at flow rates of about 5 microL/min to about 2 mL/min, more preferably of about 0.05 mL/min to about 1 mL/min, even more preferred of about 0.1 mL/min to about 0.5 mL/min, even more preferred of about 0.3 mL/min to about 0.4 mL/min, most preferred of about 0.35 mL/min.

In yet other embodiments the oligonucleotides of this invention are used for the prophylaxis and/or the treatment of a disease selected from the group of cancer, metastases, disease of the nervous system, and immunosuppression.

In preferred embodiments, cancer, metastasis, nervous system, and/or immunosuppression are treated with the respective oligonucleotides hybridizing with mRNA of the targets TGF-beta1, TGF-beta2, TGF-beta3, VEGF, interleukin-10, c-jun, c-fos and/or prostaglandin E2, even more preferred are sequences identified in the sequence listing with SEQ ID NOs 1-93. Preferred sequences hybridizing with the mRNA of TGF-beta1 are identified in the sequence listing with SEQ ID NOs 1-4, most preferred is SEQ ID NO 2. Preferred sequences hybridizing with the mRNA of TGF-beta2 are identified in the sequence listing with SEQ ID NOs 5-8, most preferred is SEQ ID NO 5. Preferred sequences hybridizing with the mRNA of TGF-beta3 are identified in the sequence listing with SEQ ID NOs 9-38. Preferred sequences hybridizing with the mRNA of prostaglandin E2 are identified in the sequence listing with SEQ ID NOs 39-49. Preferred sequences hybridizing with the mRNA of interleukin 10 are identified in the sequence listing with SEQ ID NOs 57-76. Preferred sequences hybridizing with the mRNA of c-jun are identified in the sequence listing with SEQ ID NOs 78-83. Preferred sequences hybridizing with the mRNA of c-jun are identified in the sequence listing with SEQ ID NOs 85-93.

Another embodiment of a disease of the nervous system is the amyotrophic lateral sclerosis. In a preferred embodiment the neuronal injuries are treated with the respective oligonucleotides hybridizing with m-RNA of the targets c-jun or j-fos, even more preferred are c-jun sequences identified in the sequence listing with SEQ ID NOs 78-83 respectively c-fos sequences identified in the sequence listing with SEQ ID NOs 85-93.

In one embodiment the pharmaceutical preparation is administered with an application system. A preferred application system comprises a portable pump, connected with flexible tubes to a port system. The port system is connected to an infusion catheter surgically implanted into the center of a tumor, a tissue or ending in a body cavity. In another embodiment several infusion catheters are used for infusing the pharmaceutical preparation. In yet other embodiments the infusion catheters are positioned not in the center of the tumor or tissue, but are positioned in the margin of the tissue and/or tumor infused with the pharmaceutical preparation. Application systems usable for this invention are also described in the international patent application PCT/EP 2004/004211 herein incorporated by reference. The total volume per day of the pharmaceutical preparation preferably infused into tumors, tissues or the body cavities selected from joint cavity or ventricular space vary from about 0.15 mL/d to about 0.15 L/d, more preferred from about 0.7 mL/d to about 0.07 L/d, even more preferred from about 1.2 mL/d to about 0.06 L/d, even more preferred from about 2 mL/d to about 0.03 L/d, even more preferred from about 3 mL/d to about 15 mL/d, and most preferred they are about 5.6 mL/d or about 11 mL/d.

In another embodiment the total volume of pharmaceutical preparation preferably infused into large body cavities such as intraperitoneal space or the pleural space are about 5 mL/d to about 3 L/d, more preferred about 0.05 L/d to about 1.5 L/d, even more preferred about 0.15 L/d to about 1 L/d, even more preferred about 0.4 L/d to about 0.6 L/d, most preferred are about 0.5 L/d.

In another embodiment the total amount of oligonucleotide applied into tumors, tissues or the body cavities selected from joint cavity or ventricular space by means of this invention is about 0.15 nmol to about 3 micromol, more preferred about 1 nmol to about 2 micromol, even more preferred about 0.01 micromol to about 1 micromol, even more preferred about 0.02 micromol to about 0.1 micromol, and most preferred about 0.224 micromol, about 0.112 micromol, about 0.056 micromol, or about 0.028 micromol.

In the most preferred embodiment these amounts are administered into a brain tumor, in one preferred embodiment the brain tumor is an astrocytoma, including glioblastoma or is an oligoastrocytoma.

For the treatment of brain tumors, oligonucleotides that can hybridize with mRNA of TGF-beta are preferred, more preferred are the sequences identified in the sequence listing with SEQ ID NOs 1 to 38. More preferred are oligonucleotides hybridizing with TGF-beta2, even more preferred are sequences identified in the sequence listing with SEQ ID NOs 5 to 8. In a very preferred embodiment, the oligonucleotide is identified in the sequence protocol by SEQ ID NO 5. In one preferred embodiment SEQ ID NO 5 is administered in the form of its sodium salt having a molecular weight of 6142.4 g, respectively 7115.3 g as hydrate, comprising about 54 molecules of crystal water per oligonucleotide.

In yet another embodiment the total amount of oligonucleotide applied into large body cavities such as intraperitoneal cavity or pleural cavity by a pharmaceutical preparation of this invention is about 0.005 micromol to about 0.05 mmol, more preferred about 0.05 micromol to about 0.025 mmol, more preferred about 0.1 micromol to about 0.01 mmol, and most preferred about 10 micromol, about 5 micromol or about 2.5 micromol.

In another embodiment the total amount of oligonucleotide applied into tumors, tissues or the body cavities selected from joint cavity or ventricular space by means of this invention is about 7.5 nmol to about 22.5 micromol, more preferred about 50 nmol to about 10 micromol, even more preferred about 0.1 micromol to about 5 micromol, even more preferred about 0.4 micromol to about 1 micromol, and most preferred about 0.21 micromol, about 0.28 micromol or about 0.35 micromol.

In a more preferred embodiment the respective amount is administered into a brain tumor, the most preferred embodiment of the brain tumor is astrocytoma, including glioblastoma or oligoastrocytoma.

In yet another embodiment the total amount of oligonucleotide applied into large body cavities such as intraperitoneal cavity or pleural cavity by a pharmaceutical preparation of this invention is about 0.25 micromol to about 0.45 mmol, more preferred about 1 micromol to about 0.5 mmol, more preferred about 0.01 mmol to about 0.1 mmol, and most preferred about 50 micromol, about 40 micromol or about 30 micromol.

In one embodiment the pharmaceutical preparation of this invention is administered into a tumor, a tissue or a body cavity for about 4 hours to about 8 hours, about 8 hours to about 16 hours, about 16 hours to about 24 hours, about 24 hours to about 36 hours, about 36 hours to about 2 days, about 2 days to about 3 days, about 3 days to about 5 days, about 5 days to about 8 days, about 8 days to about 11 days, and about 11 days to about 15 days. This period of time is also referred to as course. In a preferred embodiment the pharmaceutical preparation is administered over about 3 to about 8 days. The period of 4 days and 7 days is preferred for the treatment of brain tumor, where the most preferred embodiment of the brain tumor is astrocytoma, including glioblastoma, or oligoastrocytoma.

In other embodiments the oligonucleotides in a pharmaceutical preparation are administered at a plurality of times, in other words a course as defined above is repeated at plurality of times, preferring 2 to 20 times. In preferred embodiments the procedure is repeated one to twelve times, e.g. twice to three times, four times to five times, six times to seven times, eight times to nine times, ten times to eleven times, twelve times to thirteen times, fourteen times to fifteen times, sixteen times to seventeen times, eighteen times to nineteen times, or twenty times.

All courses may have the same duration or may vary. In some embodiments the time between two courses is between about 1 day to about 2 days, about 2 days to about 3 days, about 4 days to about 5 days, about 5 days to about 7 days, about 8 days to about 10 days, about 10 days to about 2 weeks, about 2 weeks to about 3 weeks, about 3 weeks to about 4 weeks, about 4 weeks to about 6 weeks, and about 6 weeks to about 12 weeks. In a preferred embodiment the time between two courses varies between about 2 days and 8 weeks, more preferred about 4 days to about 4 weeks, even more preferred about 6 days to about 12 days.

In one preferred embodiment the oligonucleotide dissolved in a physiological (=isotonic) solution is administered over 7 days and then during the next 7 days no oligonucleotide is administered. This course was repeated several times.

In yet another embodiment the pharmaceutical preparation comprises at least one oligonucleotide and in addition at least one further adjuvant. For more details about adjuvants, also referred to as immunostimulants, see also EP 1 089 764. In a preferred embodiment the adjuvants is an oligonucleotide comprising an CpG-motiv. For further details about CpG motives see also Krieg 2002.

Preferred embodiments of the pharmaceutical preparations of this invention are used in mammals, where the preferred embodiment of mammal is a human. Besides being useful in human treatment, the present invention is also useful for other subjects including veterinary animals, exotic animals and farm animals, including mammals, rodents, and the like. Mammals include humans, horses, dogs, pigs, cats, or primates (for example, a monkey, a chimpanzee, or a lemur). Rodents include rats, mice, squirrels, or guinea pigs.

In one embodiment the pharmaceutical preparation with the oligonucleotide of this invention is administered to a mammal by first dissolving the oligonucleotide with a concentration of about 1 to 150 microM in a pharmaceutically acceptable carrier to a solution and then administering said solution at a flow rate of about 0.1 microL/min to about 2 mL/min to a tissue, a tumor, or a body cavity of the mammal. Further preferred concentrations, flows and sequences are given above in this invention.

In one embodiment the pharmaceutical preparation with at least one oligonucleotide of this invention for the treatment of tumors and/or metastases is administered to a mammal at an amount resulting in a concentration of this oligonucleotide ranging from about 1 to about 50 microgram per 1 $cm^3$ of the respective tumor.

In yet another embodiment the pharmaceutical preparation is administered in a way that the concentration of the oligonucleotide is about 2 to about 20 microgram per 1 $cm^3$ of tumor tissue per day, more preferred are about 3 to about 10 microgram per 1 $cm^3$ of tumor tissue per day.

The pharmaceutical preparation of the present invention may be administered in a number of ways depending upon whether local or systemic treatment is desired and upon the area to be treated. The pharmaceutical composition of the present invention may be administered by infusion directly into a tissue, tumor and/or a body cavity. Administering the pharmaceutical preparations of the present invention may be accomplished by any means known to a person skilled in the art. Routes of administration include but are not limited to parenteral (e.g. intramuscular), intraperitoneal, intraventricular, intracerebral, intratumoral, intracerebroventricular, intrathecal, intrauterine, infusion and injection into bladder, and pleura.

Pharmaceutical preparations include fluid pharmaceutical preparations containing the oligonucleotide in a concentration of about 1 microM to about 25 microM. In another preferred embodiment the pharmaceutical preparation contains the oligonucleotide in a concentration of about 50 microM to about 150 microM. More preferred concentrations are given above. Such preparations may include sterile aqueous solutions that may also contain buffers, diluents and other suitable additives, such as, but not limited to, penetration enhancer, acceptable carriers or excipients. The term pharmaceutical preparation implies that the liquids or substances of this composition are pure and/or combined with pharmaceutically acceptable carriers.

The term pharmaceutically acceptable carrier means one or more compatible liquid filler, diluents or encapsulating substances that are suitable for administration to a human or other mammal. The term "carrier" denotes an organic or inorganic ingredient, natural or synthetic, with which the active ingredient is combined to facilitate the application. The components of the pharmaceutical preparations also are capable of being combined with the compounds of the present invention, and with each other, in such a manner that there is no interaction which would substantially impair the desired pharmaceutical efficacy. Such carriers enable the oligonucleotides of the invention to be formulated as liquids, gels, syrups, slurries, suspensions, emulsions.

As described above the pharmaceutical compositions may also include microcapsules, nanocapsules, micro- and nano-spheres, emulsions and suspensions, oligonucleotides coated onto microscopic gold particles or preparations with protracted release of oligonucleotides, in whose preparation excipients and additives and/or auxiliaries such as disintegrants, binders, coating agents, swelling agents, lubricants, or solubilizers are customarily used.

For the infusion into the stomach, intestine, colon, or rectum an enema is useful.

For a brief review of present methods of drug delivery, see Langer (1990), which is incorporated herein by reference.

In yet another embodiment, the oligonucleotides are present in pharmaceutical carriers for parenteral administration by infusion. Formulations for infusion may be presented in unit dosage form with an added preservative. The pharmaceutical compositions take such forms as suspensions, solutions or emulsions in oily or aqueous vehicles, and contain formulatory agents such as suspending, stabilizing and/or dispersing agents.

In one embodiment, pharmaceutical carriers for parenteral administration include aqueous solutions of the oligonucleotides in water-soluble form. In one preferred embodiment the oligonucleotide is dissolved in a physiological (isotonic) solution, more preferred 0.9% sodium chloride solution.

In yet another embodiment a suspension of the compounds is prepared as appropriate oily infusion. Suitable lipophilic solvents or vehicles include fatty oils such as sesame oil, or synthetic fatty acid esters, such as ethyl oleate or triglycerides, or liposomes. Aqueous infusion suspensions comprise substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In yet another embodiment, the oligonucleotides may be in powder form for reconstitution with a suitable vehicle, e.g., sterile pyrogen-free water, before use. In other embodiments the oligonucleotide is reconstituted with an isotonic solution. Isotonic solution is any aqueous solution with an osmotic pressure as high as the osmotic pressure of the body. Commonly used are solutions of salts, sugars and so on. In preferred embodiments the isotonic solution is a 0.9% sodium chloride solution or a Ringer-lactate solution (e.g. DAB7).

In yet another embodiment, the active compounds may be in form of a concentrate for dilution with a suitable vehicle, e.g., sterile pyrogen-free water, before use.

In yet another embodiment, the compounds are formulated in rectal or vaginal compositions such as suppositories or retention enemas or tablets, e.g., containing conventional suppository bases such as cocoa butter or other glycerides.

In yet another embodiment, the compounds are formulated as a depot preparation. In one embodiment such long acting preparations are formulated with suitable polymeric or hydrophobic materials (for example as an emulsion in an acceptable oil) or ion exchange resins, or as sparingly slow soluble derivatives, for example as a sparingly slow soluble salt.

In other embodiments, delivery systems include time-release, delayed release, or sustained release delivery systems. Such systems can avoid repeated administrations of the compounds, increasing convenience to the subject and the physician. Many types of release delivery systems are available and known to those of ordinary skill in the art.

In one embodiment, the delivery systems include polymer based systems such as poly(lactide-glycolide), copolyoxalates, polycaprolactones, polyesteramides, polyorthoesters, polyhydroxybutyric acid, and polyanhydrides, more preferred polyanhydrides with molecular weight of more than 20.000 Da. In one preferred embodiment the polyanhydride is a polycondensation of dicarbonic acids with high molecular weight. More details see also EP 0260415. Microcapsules of the foregoing polymers containing drugs are described in, for example U.S. Pat. No. 5,075,109.

In another embodiment, improvement of oligonucleotide uptake has been achieved with different systems of vectorization including liposomes (neutral, cationic, immunoliposome), micro- and nanoparticles, polymers, or covalent attachment to a carrier (C. Lefebure et al. 1995). Lipid-mediated transfection has also been used to deliver oligonucleotides (Wang and Martini 1996). In another embodiment the delivery systems include non-polymer systems that are e.g. lipids including sterols such as cholesterol, cholesterol esters and fatty acids or neutral fats such as mono-, di- and triglycerides, hydrogel release systems, sylastic systems, peptide based systems, and the like.

Specific examples include, but are not limited to: (a) erosional systems in which an agent of the invention is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686.

In still other embodiments, the oligonucleotides are formulated with GELFOAM®, a commercial product consisting of modified collagen fibers that degrade slowly.

In one embodiment the pharmaceutical compositions also comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

In one embodiment the oligodeoxynucleotides are administered neat or in the form of a pharmaceutically acceptable salt. The salts have to be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

In another embodiment the pharmaceutical composition further comprises at least one buffer and/or at least one preservative.

In one embodiment suitable buffering agents include but are not limited to acetic acid and a salt (1-2% w/v), citric acid and a salt (1-3% w/v), boric acid and a salt (0.5-2.5% w/v), and phosphoric acid and a salt (0.8-2% w/v).

Suitable preservatives include benzalkonium chloride (e.g. 0.003-0.03% w/v), chlorobutanol (e.g. 0.3-0.9% w/v), parabens (e.g. 0.01-0.25% w/v), and thiomersal (e.g. 0.004-0.02% w/v).

In yet another embodiment the pharmaceutical compositions also include penetration enhancers in order to enhance the alimentary delivery. Penetration enhancers may be classified as belonging to one of five broad categories, i.e., fatty acids, bile salts, chelating agents, surfactants, and non-surfactants (Lee et al. 1991, Muranishi 1990). One or more penetration enhancers from one or more of these broad categories may be included. Various fatty acids and their derivatives which act as penetration enhancers include, for example, oleic acid, lauric acid, capric acid, myristic acid, palmitic acid, stearic acid, linoleic acid, linolenic acid, dicaprate, tricaprate, recinleate, monoolein (1-monooleoyl-rac-glycerol), dilaurin, caprylic acid, araichidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc.) (Lee et al. 1991, Muranishi 1990, El-Hariri et al. 1992). Examples of some presently preferred fatty acids are sodium caprate and sodium laurate, used singly or in combination at concentrations of 0.5 to 5%.

The physiological roles of bile include the facilitation of dispersion and absorption of lipids and fat-soluble vitamins (Brunton 1996). Various natural bile salts, and their synthetic derivatives, act as penetration enhancers. Thus, the term "bile salt" includes any of the naturally occurring components of bile as well as any of their synthetic derivatives. A presently preferred bile salt is chenodeoxycholic acid (CDCA) (Sigma Chemical Company, St. Louis, Mo.), generally used in concentrations of 0.5 to 2%. Complex formulations comprising one or more penetration enhancers may be used. For example, bile salts may be used in combination with fatty acids to make complex formulations. Preferred combinations include CDCA combined with sodium caprate or sodium laurate (generally 0.5 to 50%).

In one embodiment additionally chelating agents are used that include, but are not limited to, disodium ethylenediaminetetraacetate (EDTA), citric acid, salicylates (e.g., sodium salicylate, 5-methoxysalicylate and homovanillate), N-acyl derivatives of collagen, laureth-9 and N-amino acyl derivatives of beta-diketones (enamines) (Lee et al. 1991, Muranishi 1990, Buur et al. 1990). Chelating agents have the added advantage of also serving as DNase inhibitors.

In yet another embodiment additionally surfactants are used. Surfactants include, for example, sodium lauryl sulphate, polyoxyethylene-9-lauryl ether and polyoxyethylene-20-cetyl ether (Lee et al. 1991), and perfluorochemical emulsions such as FC-43 (Takahashi et al. 1988). Non-surfactants include, for example, unsaturated cyclic ureas, 1-alkyl- and 1-alkenylazacyclo-alkanone derivatives (Lee et al. 1991), and non-steroidal anti-inflammatory agents such as diclofenac sodium, indomethacin, and phenylbutazone (Yamashita et al. 1987).

In one embodiment, the pharmaceutical compositions of the present invention additionally contain other adjunct components conventionally found in pharmaceutical compositions, at their art-established usage levels. Thus, for example, the compositions may contain additional compatible pharmaceutically active materials such as, e.g., antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents, and stabilizers. However, such materials, when added, should not unduly interfere with the biological activities of the components of the compositions of the invention.

The present invention can be used for the described drug application in any tissue of the subject where this method is indicated. Such tissues include, for example, bile duct, bladder, bone, bone marrow, brain, breast, colon, endometrium, epithelium, gall, gall bladder, head, head and neck, heart, intestine, joints, kidney, larynx, liver, lung, lymphatic node, lymphatic vessels, muscle, oesophagus, ovary, pancreas, prostate, rectum, urinary duct, skin and its layers, spleen, stomach, testis, thymus, thyroid, tonsil, or uterus.

The respective tumor of a tissue also referred to as tumor or neoplasm comprises adamantinoma of long bones, adenoma, ameloblastoma, astrocytoma, bile duct carcinoma, bladder carcinoma, bone carcinoma, bone marrow carcinoma, brain tumor, breast cancer, bronchogenic carcinoma, cervical cancer, cervical cancer of uteri, chondroma, choriocarcinoma, colon carcinoma, colorectal carcinoma, cystadeno, carcinoma, embryonal carcinoma, endometrial cancer, ependymoma, esophageal cancer, fibroma, follicular thymoma, gallbladder cancer, gastric cancer, glioblastoma, glioma, head and neck cancer, cancer of the heart, hepatocellular cancer, cancer in the intraperitoneal cavity, cancer of the intestine, carcinoma of the kidney, larynx cancer, lipoma, liver carcinoma, lung carcinoma, cancer of the lymphatic node, cancer of the lymphatic vessels, malignant glioma, mesenthelioma, menigioma, medullary carcinoma, myoma, neuroblastoma, non-small-cell bronchogenic/lung carcinoma, oesophagus cancer, osteosarcoma, ovarian cancer, pancreas carcinoma, papillary carcinoma, papillary adenocarcinoma, papillar thymoma, pheochromocytoma, prostate cancer, rectal cancer, renal cancer, renal cell carcinoma, urinary duct carcinoma, sebaceous gland carcinoma, seminoma, skin cancer, small-cell lung carcinoma, small intestine carcinoma, soft tissue cancer, spleen carcinoma, squamous cell carcinoma, stomach carcinoma, teratoma, testicular carcinoma, testis carcinoma, thymoma, thyroid cancer, thyroid gland tumors, and corpus cancer of the uterus.

The expressions tumor, cancer, and neoplasm are used synonymously in the context of this invention.

EXAMPLES

In this application the results of local toxicity studies in animals as well as clinical studies in patients are reported. All these studies have been performed in accordance with current Good Clinical Practice (GCP) guidelines and have been approved by local ethics committees. Patient studies furthermore followed the current international declaration of Helsinki for human experimentation.

Example 1

Local Toxicity Studies after Intrathecal Bolus Injection in Rabbits

The local safety and tolerability of a pharmaceutical preparation comprising the antisense oligonucleotide against mRNA of TGF-beta2 identified by SEQ ID NO 5 was demonstrated in local toxicity studies applying said oligonucleotide intrathecally into rabbits as a bolus. Two studies were carried out each with eight rabbits (2/gender/treatment group) administering 0.1 ml of a 14 microM or a 500 microM solution of said oligonucleotide in normal saline, respectively, by single intrathecal bolus injection into the subarachnoidal space of the lumbar region. The control groups received 0.9% NaCl solution in the same manner. Local reactions were inspected macroscopically 2, 6, and 30 hours after administration. Six and 30 hours after administration 1 animal/gender/group was sacrificed. Brain tissue samples (thickness approx. 5 microm) were examined histologically.

In none of the rabbits any clinical signs of toxicity or macroscopically visible changes were noted for both concentrations. In both studies the histopathological examination revealed no substance-related histomorphological lesions in the subarachnoidal space of the lumbar region. No substance-related changes were observed in the gray and white matter of the spinal cord. The nerve trunk and nerve cells did not show any abnormalities.

One control rabbit (0.9% sodium chloride) showed moderate to marked hemorrhage in the leptomeninx and in the nerve trunk, a mild malacia and infiltration of neutrophilic granulocytes and moderate fibrinous deposits.

All animals except one control rabbit (0.9% sodium chloride) revealed mild to moderate hemorrhages in the white matter, lumen of the central canal, gray matter and/or subarachnoidal space. All these changes are considered to be due to the mechanical damage caused by the intrathecal injection and, hence, are not substance-related.

Conclusively, the oligonucleotide identified with the sequence ID No. 5 revealed an excellent local tolerability in rabbits after intrathecal bolus application up to a concentration of 500 microM of the oligonucleotide solution.

Example 2

Local Toxicity Study after Intrathecal Bolus Injection in Cynomolgus Monkeys The intrathecal bolus application described in example 1 was repeated in cynomolgus monkeys to investigate the safety and local tolerance of a solution of the antisense oligonucleotide with sequence ID No. 5 in a higher developed animal. Due to the excellent local tolerability of the 500 microM solution of the said antisense oligonucleotide against the mRNA of TGF-beta2 only this one concentration was investigated.

Two cynomolgus monkeys were treated with 0.1 mL of a 500 microM solution (0.9% sodium chloride) of an oligonucleotide hybridizing with the mRNA of TGF-beta2 identified in the sequence protocol by SEQ ID NO 5 by single intrathecal bolus injection into the subarachnoidal space of the lumbar region. Local reactions were inspected macroscopically 2, 6 and 30 hours after administration and then the animals were sacrificed. Brain tissue samples (thickness approx. 5 microm) were examined histologically.

No clinical signs of toxicity and no macroscopically visible changes were noted in the monkeys. The histopathological examination revealed no substance-related histomorphological lesions in the subarachnoidal space of the lumbar region. No changes were noted in the gray and white matter of the spinal cord. The nerve trunk and nerve cells did not show any abnormalities. Both monkeys revealed a mild focal mixed-cell infiltration of the leptomeninx, associated with a mild focal mineralization in the region of the inflammation. The changes are not considered to be substance-related but due to the mechanical damage caused by the intrathecal injection.

Conclusively, as observed before in the experiments with rabbits described in example 1 the said oligonucleotide revealed also in monkeys an excellent local tolerability when applied as a highly concentrated 500 microM solution. Local toxic effects could not be observed.

Example 3

Local Toxicity Study after Continuous Intracerebral Infusion in Rabbits

Based on the excellent local tolerability of the 500 microM solution of the oligonucleotide identified by the SEQ ID NO. 5 after intrathecal bolus application in rabbits and monkeys described in example 1 and 2, a long-term continuous intracerebral infusion of a 500 microM solution of said oligonucleotide over seven days was investigated in rabbits with regards to local toxicity.

Eight rabbits (2/gender/treatment group) were treated with a 500 microM solution (0.9 sodium chloride) of an antisense oligonucleotide against the mRNA of TGF-beta2 identified in the sequence listing by SEQ ID NO 5 by continuous infusion into the cerebral parenchyma of the brain or with 0.9% sodium chloride solution as control, respectively. The infusion was performed at a flow rate of 1 microL/h for a period of 7 days employing a subcutaneously implanted osmotic pump. Clinical signs and mortality were checked and recorded daily. 6 and 30 hours after the end of infusion 1 animal/gender/group was sacrificed. Brain tissue samples (thickness approx. 5 microm) were examined histologically.

In none of the rabbits any clinical signs of toxicity or macroscopically visible changes were noted.

In both groups, substance-treated and control group, focal degeneration and necrosis of the nervous tissue with proliferation of the glial cells, and the occurrence of a homogeneous yellow-green material and dark neurons as well as mild to moderate haemorrhages were noted. These lesions are considered to be related to the continuous infusion process and to the immersion fixation and, therefore, are not substance-related. There was no difference between the sacrifice 6 and 30 hours after the end of the application.

Conclusively, a 500 microM solution of said oligonucleotide when applied intracerebrally with a flow of 1 microL/h was well tolerated in rabbits.

Example 4

Effect of Oligonucleotide Concentration in the Treatment of Malignant Glioma Patients The evaluation herein was performed to compare the 40 microM and the 80 microM dosing of TGF-beta2 specific oligonucleotide in malignant glioma patients refractory to or recurrent after standard therapy (surgery, radiotherapy, and different therapies with antineoplastic substances).

The antisense oligonucleotide against the mRNA of TGF-beta2 identified by SEQ ID NO 5 was administered by a catheter intratumorally into the center of the targeted tumor lesion. Patients were treated with a 40 microM (4 patients) and a 80 microM (13 patients) solution of said oligonucleotide (0.9% sodium chloride) at a flow rate of 4 microL/min and 8 microL/min, respectively.

Table No. 1 shows the comparison between the mean survival of the patients and the number of patients with complete remission after treatment with the 40 microM and the 80 microM solution of the antisense oligonucleotide against the mRNA of TGF-beta2 identified in the sequence protocol by the SEQ ID NO 5.

TABLE NO. 1

| Dose | Number of patients | Survival after start of AP 12009 (median, weeks) | Number of patients with complete remission |
|---|---|---|---|
| 40 microM | 4 | 9.6 | 0 |
| 80 microM | 13 | 35.9 | 1 |

Patients treated with the 40 microM solution showed a median of about 9.6 weeks of survival after start of the treatment with said oligonucleotide, whereas patients treated with the 80 microM solution showed a median of about 35.9 weeks of survival after start of the treatment with said oligonucleotide. However, only in the group treated with the 80 microM solution patients with complete remission were observed.

The chosen concentrations of the oligonucleotide solutions as well as the flow rates were much lower compared to the conditions used in the animal experiments described in the example 3 where up to a oligonucleotide solution with 500 microM and a flow rate of 1 microL/h no local toxic effects were observed.

Example 5

Effect of Low Concentrated Oligonucleotide Solutions in the Treatment of Malignant Glioma Patients The evaluation herein was performed to compare the low concentrated 2.5 microM and the 10 microM dosing of TGF-beta2 specific oligonucleotide in malignant glioma patients refractory to or recurrent after standard therapy (surgery, radiotherapy, and different therapies with antineoplastic substances).

The antisense oligonucleotide against the mRNA of TGF-beta2 identified by the SEQ ID NO 5 was administered by a catheter intratumorally into the center of the targeted tumor lesion. Patients were treated with a 2.5 microM (3 patients) and a 10 microM (4 patients) solution of said oligonucleotide (0.9% sodium chloride) at a flow of 4 microL/min.

Table No. 2 shows the comparison between the mean survival of the patients and the number of patients with complete remission after treatment with the 2.5 microM and the 10 microM solution of the oligonucleotide hybridizing with the mRNA of TGF-beta2 identified in the sequence protocol by SEQ ID NO 5.

TABLE NO. 2

| Dose | Number of patients | Survival after start of AP 12009 (mean, weeks) | Number of patients with complete remission |
|---|---|---|---|
| 2.5 microM | 3 | 52 | 0 |
| 10 microM | 4 | 44 | 1 |

Surprisingly, the low concentrated solutions of said oligonucleotide showed a high mean survival of the treated patients when the solution at the flow rate of 4 microL/min was administered. Patients treated with the 2.5 microM solution showed a mean of about 52 weeks of survival after start of the treatment with said oligonucleotide. Patients treated with the 10 microM solution showed a mean of about 44 weeks of survival after start of the treatment with said oligonucleotide. However, only in the group treated with the 10 microM solution patients with complete remission were observed.

Example 6

Effect of Oligonucleotide Concentration in the Treatment of Anaplastic Astrocytoma Patients The evaluation herein was performed to compare the 2.5 microM, 10 microM and the 80 microM dosing of TGF-beta2 specific oligonucleotide in anaplastic astrocytoma patients refractory to or recurrent after standard therapy (surgery, radiotherapy, and different therapies with antineoplastic substances).

The antisense oligonucleotide against the mRNA of TGF-beta2 identified in the sequence protocol by SEQ ID No. 5 was administered by a catheter intratumorally into the center of the targeted tumor lesion. Patients were treated with a 2.5 microM, a 10 microM and a 80 microM solution of said oligonucleotide (0.9% sodium chloride) at a flow rate of 4 microL/min and 8 microL/min, respectively. The oligonucleotide has a molecular weight of 6142.4 g/M as sodium salt and 7115.3 g/M as sodium salt hydrate. Therefore, the total amount of the oligonucleotide applied was about 344 microg/d (sodium salt), respectively 398 microg/d (sodium salt comprising crystal water).

Case Reports:

Patient #1 diagnosed with anaplastic astrocytoma was treated with a 2.5 microM solution (0.9% sodium chloride) of the antisense oligonucleotide against the mRNA of TGF-beta2 with the SEQ ID No. 5 applied with a continuous flow of 4 microL/min for 4 days (2 cycles) directly into the tumor by a catheter. Patient #1 showed a survival of about 146 weeks after treatment which was surprisingly high compared to the standard therapy with temozolomide resulting in a median survival of about 42 weeks (Theodosopoulos et al. 2001). Patient #4 diagnosed with anaplastic astrocytoma (4 tumor lesions/metastases, including two on the contralateral side) was treated with a 10 microM solution (0.9% sodium chloride) of the antisense oligonucleotide against the mRNA of TGF-beta2 with the SEQ ID NO 5 which was applied at a continuous flow rate of 4 microL/min for 4 days directly into the largest tumor by a catheter. Patient #17 diagnosed with anaplastic astrocytoma was treated with an 80 microM solution (0.9% sodium chloride) of the oligonucleotide hybridizing with the mRNA of TGF-beta2 identified in the sequence protocol by the SEQ ID No. 5 at a flow rate of 8 microL/min.

TABLE NO. 3

| Patient number | Number of cycles | Concentration | Months (from baseline*) of maximal tumor size | Tumor volume after 17 months of observation |
|---|---|---|---|---|
| #4 | 1 | 10 microM | 2.5 | 12 cm$^3$ |
| #17 | 12 | 80 microM | 9.7 | 27 cm$^3$ |

*baseline is the startpoint when treatment with the pharmaceutical preparation comprising the oligonucleotide, identified in the sequence listing with SEQ ID NO 5, was started.

Patient #4 treated with a pharmaceutical preparation comprising 10 microM of the oligonucleotide identified in the sequence protocol with SEQ ID NO 5 as well as the patient #17 treated with the same pharmaceutical preparation with 80 microM of said oligonucleotide showed nearly the same tumor volume at the baseline. Patient #4 reached the maximum of tumor size of about 58 cm$^3$ after about 2.5 month, whereas in patient #17 tumor growth to a maximum of 66 cm$^3$ could be observed up to about 9.7 months.

After about 17 months of observation the tumor volume of patient #4 was reduced to about 12 cm$^3$, whereas the tumor of patient #17 still had about double the volume (27 cm$^3$).

Additionally, compared to the 10 microM dosed patient (#4) already showing tumor regression only after one application cycle, the 80 microM dosed patient (#17) needed 12 cycles to achieve tumor regression.

Example 7

Effect of Oligonucleotide Concentration in the Treatment of Malignant Glioma Patients by Application with a Flow of 4 microL/min The evaluation herein was performed to compare the 10 microM and the 80 microM dosing of a TGF-beta2 specific oligonucleotide applied at a flow rate of 4 microL/min in malignant glioma patients refractory to or recurrent after standard therapy (surgery, radiotherapy, and different therapies with antineoplastic substances).

The antisense oligonucleotide against the mRNA of TGF-beta2 identified by SEQ ID NO 5 was administered as a continuous intratumoral high-flow microperfusion. Patients were treated with 10 microM (9 patients) and 80 microM (10 patients) oligonucleotide solution (0.9% sodium chloride) with a flow of 4 microL/min for seven days followed by a seven day drug-free interval (=one cycle). Patients were treated with up to 12 cycles.

TABLE NO. 4

| Dose | Number of patients | Number of patients with reduction in tumor size | Patients with progressive disease (%) | Difference tumor size to baseline, last visit (median, mm³) |
|---|---|---|---|---|
| 10 microM | 9 | 5 | 33.3% | −264 |
| 80 microM | 10 | 2 | 50% | 19940 |

Table No. 4 depicts a comparison of tumor size reduction between baseline and last visit, the number of patients with progressive disease and with a reduction in tumor size between malignant glioma patients treated with a 10 microM and a 80 microM solution of the antisense oligonucleotide against the mRNA of TGF-beta2 identified by SEQ ID NO 5 applied at a flow rate of 4 microL/min.

From the group of patients treated with the 10 microM solution of said oligonucleotide administered at a flow rate of 4 microL/min only 33.3% of the patients showed a progressive disease compared to 50% of the patients treated with the 80 microM solution of said oligonucleotide at the same flow rate. Five from nine patients showed a reduction in tumor size in the 10 microM group compared to only 2 from 10 patients in the 80 microM group. The difference in tumor size between baseline and last visit was reduced to −264 mm³ (median) in the 10 microM group. In contrast, the group receiving the 80 microM solution showed an increase in tumor size to 19940 mm³ (median).

Example 8

Effect of Oligonucleotide Concentration in the Treatment of Anaplastic Astrocytoma Patients The evaluation herein was performed to compare the 10 microm and the 80 microm dosing of a TGF-beta2 specific oligonucleotide in anaplastic astrocytoma patients, refractory to or recurrent after standard therapy (surgery, radiotherapy, and different therapies with antineoplastic substances). Patients were selected as described in example 2.

The antisense oligonucleotide against mRNA of TGF-beta2 identified by SEQ ID NO 5 was administered as a continuous intratumoral high-flow microperfusion. Patients were treated with 10 microm (11 patients) and 80 microM (11 patients) solution (0.9% sodium chloride) of said oligonucleotide at a flow rate of 4 microL/min for seven days followed by a seven day drug-free interval (=one cycle). Patients were treated with up to 12 cycles.

The number of anaplastic astrocytoma patients with symptoms due to disease progression (Aes grade 1 to 4 and SAE) in the group of patients treated with the 10 microm solution of said oligonucleotide was surprisingly low compared to patients infused with the 80 microM solution as shown in FIG. 1. Only one patient out of eleven of the 10 microM group was affected compared to nine out of eleven patients of the 80 microm group. In the 10 microm group only grade 3 symptoms were observed. In the 80 microM group 6 from the 9 symptoms were graded/judged as SAEs (serious adverse events).

Example 9

Compatibility of the Flow Rate in the Treatment of Malignant Glioma Patients

The antisense oligonucleotide against the mRNA of TGF-beta2 identified in the sequence listing by SEQ ID NO 5 was administered as a continuous intratumoral high-flow microperfusion. Patients were treated with a 10 microM solution of said oligonucleotide at a flow rate of 4 microL/min, and 40 microL/min applying 5.75 mL and 57 mL in 24 h, respectively. Each flow rate was well tolerated demonstrating the safety of application of a 10 microM solution up 40 microL/min in patients.

Example 10

Effect of Oligonucleotide Concentration in the Treatment of Malignant Glioma Patients The evaluation herein was designed to test the 10 microm dosing of a TGF-beta2 specific oligonucleotide in anaplastic astrocytoma patients refractory to or recurrent after standard therapy (surgery, radiotherapy, and different therapies with antineoplastic substances). The antisense oligonucleotide against the mRNA of TGF-beta2 identified by SEQ ID NO 5 was administered as a continuous intratumoral high-flow microperfusion. Patients were treated with 10 microM oligonucleotide solution (0.9% sodium chloride) with a flow rate at 4 microL/min for seven days followed by a seven day drug-free interval (=one cycle). Patients were treated with up to 12 cycles.

FIG. 2 shows the decrease in tumor size in three anaplastic astrocytoma patients treated with a 10 microM solution of said oligonucleotide applied with at a flow rate of 4 microL/min. Patient #409 (FIG. 2A) showed a reduction of tumor size of about 19 cm³ to about 7 cm³ after five months of treatment. The tumor of patient #412 (FIG. 2B) shrunk of about 39 cm³ to about 26 cm³ after only two months of treatment with the 10 microM solution of said oligonucleotide. The size of the tumor of patient #413 (FIG. 2C) reduced of about 19 cm³ to about 11 cm³ upon treatment with 10 microM solution of said oligonucleotide.

In contrast patient #17 (FIG. 2D), treated with a concentration of 80 microM of said oligonucleotide and at a flow rate of 8 microL/min showed an increased tumor growth during the first 5 months of about 8 cm³ to about 18 cm³.

Example 11

Survival Data of Patients with Anaplastic Astrocytoma

A multi-national randomized active-controlled clinical phase II study was performed. Eligible patients had AA, WHO grade III refractory to or recurrent after standard therapy (surgery, radio- and chemotherapy) and were not suitable for another tumor resection. Patients had not received antitumor therapies for 10 days prior to study entry (median: 42 days, range 10 to 295 days prior to start of treatment with the oligonucleotide). Karnofsky performance status (KPS) was at least 70%. Patients with clinically significant acute infections, major cardiovascular abnormalities or poorly controlled seizures as well as pregnant and lactating females were excluded.

A catheter was implanted in every patient and the perforated part of the catheter was placed into the solid, contrast enhancing area of the tumor lesion. The catheter was inserted through a standard burr hole into the largest tumor lesion present.

A port system was implanted into a subcutaneous pouch on the anterior chest wall. The port catheter was tunneled subcutaneously and connected to the tumor catheter, and the port to an external pump.

The oligonucleotide with SEQ ID NO 5 dissolved in 0.9% of sodium chloride solution was infused via the pump through the port into the tumor with a continuous flow. During the seven-day interval between two cycles of treatment with oligonucleotide, isotonic saline was infused at 1 microL/min. During the course of the study most of the patients received prophylactic antibiotics preoperatively, but no prophylactic steroids. The oligonucleotide was administered intratumorally as a continuous high-flow microperfusion using external pump devices, PEGASUS® Vario (PEGASUS GmbH, Kiel). The catheter and the application system were removed at the end of the whole infusion period. For safety assessment, patient follow-up was performed for 28 days. The investigators continued to collect survival data.

Survival data of 38 patients were evaluated out of which 12 patients treated with 10 microM oligonucleotide solution, 14 patients were treated with 80 microM and 12 patients in the control group received a standard chemotherapy with temozolomide or PCV (a chemotherapeutic regiment, consisting of procarbazine, CCNU, and vincristin, see below for more details).

In the 10 microM group 83.3% of the patients were under the age of 55, in the 80 microM group 85.7% and in the control group 91.7%. As age is known to be a prognostic factor influencing a patient's outcome, the control group with over 90% younger patients had a better chance of survival compared to the groups treated with the oligonucleotide, especially the group with the 10 microM concentration of oligonucleotide. Despite this worse baseline situation the group with the oligonucleotide with SEQ ID NO 5 had a much higher survival chance than in the control group or the group with 80 microM concentration of oligonucleotide. Adjusted according to age (analysis of covariance), this difference became even more significant.

Also Karnofsky's Performance Status (KPS) is known as prognostic factor. In the control group, many more patients were included with a higher (=better) KPS: KPS>80 in AP10 group 66.6% in AP80 group 71.4%, and in control group 83.3%. The gender distribution was also different. The group with 10 microM oligonucleotide had 50% males, the 80 microM group had 92.9% males, and the control group had 50% males. Gender does not seem to have an effect on survival chance, therefore no adjustment for this parameter was needed.

The results of the study are as depicted in Table No. 5 and in FIG. 6.

A typical standard PCV-cycle consists of a 29 day treatment period followed by a 4 week treatment-free period. During the 29 day treatment period CCNU, Vincristine and Procarbazine are administered according to the scheme below (Levin et al 1990):

| Day 1 | 110 mg/m2 CCNU orally |
|---|---|
| Days 8 and 29 | 1.4 mg/m2 (2 mg/m2 maximum) per day Vincristine intravenously |
| Days 8 to 21 | 60 mg/m2 per day Procarbazine orally |

TABLE NO. 5

|  | 10 micro M versus 80 microM | 10 microM versus control | 80 microM versus control |
|---|---|---|---|
| HR | 3.4 | 1.7 | 0.9 |
| HR (age)* | 3.8 | 1.8 | 0.9 |

*Hazard ratio with "age" as covariate

The Hazard Ratio (HR) compares the survival chance between two groups at any time point. Since the outcome (survival) is significantly influenced by the age difference at the beginning, this difference has to be considered by applying an analysis of covariance which adjusts the results for this difference at beginning. An age adjusted Hazard Ratio (HR (age)) of 1.8 for 10 microM versus control means that the survival chance for any single patient is 1.8 times higher when he receives SEQ ID NO 5 in a concentration of 10 microM over receiving standard chemotherapy (i.e. temozolomide or PCV=a chemotherapeutic regiment, consisting of procarbazine, CCNU and vincristin). And the survival chance is 3.8 fold higher for patients receiving SEQ ID NO 5 in a concentration of 10 microM over patients receiving this oligonucleotide in a concentration of 80 microM.

Example 12

Comparison of Different Oligonucleotide Concentrations on TGFbeta2 Secretion in A-172 Cell Line Cell culture: The human glioblastoma cell line A-172 (Accession no. CRL-1620) was established from a 53-year old man with a glioblastoma.

The A-172 tumor cells were cultivated in DMEM-medium with 4.5 g/L glucose and 10% (v/v) FCS at 37° C., 5% CO2, and 95% relative humidity according to the instructions of the Cell Line Service. To investigate TGF-□eta2 suppression, 40,000 A-172 cells/well were seeded into 12-well tissue culture plates. Six hours after seeding the supernatants were removed and replaced by a treatment solution consisting of cell culture medium containing 5 microM, 10 microM, or 80 microM of antisense oligonucleotide identified by SEQ ID NO 5. Medium of the negative control (=untreated cells) was changed without addition of SEQ ID NO 5. The exchange was repeated after 2 and 4 days. On day 7 the supernatants were collected and analyzed for secreted TGF-beta2 by using Enzyme-Linked Immunosorbent Assay (ELISA).

Methods: TGF-beta2 was quantified by a standard TGF-beta2-ELISA-Kit according to the manufacturer's instructions. The supernatants were cleared of cellular components by centrifugation (850 g, 5 min). TGF-beta2 analysis was performed with the Multiskan Ascent Type 354 200-240V plate reader using a 4 parameter logistic.

Results: The human glioblastoma cell line A-172 was tested in a set of TGF-beta2 secretion experiments to evaluate the effect of different concentrations of the antisense oligonucleotide identified by SEQ ID NO 5. A-172 cells produce TGF-beta2 under cell culture conditions. Duration of cell treatment (7 days) as well as the three different concentrations (5 microM, 10 microM, 80 microM) of SEQ ID NO 5 were chosen.

10 microM of oligonucleotide identified by SEQ ID NO 5 was found to be the best inhibitor of TGF-beta2 expression compared to 5 and 80 microM of this oligonucleotide.

REFERENCES

Buur et al., J. Control Rel., 1990, 14, 43-51
Brunton, Chapter 38 in: Goodman & Gilman's The Pharmacological Basis of Therapeutics, 9th Ed., Hardman et al. Eds., McGraw-Hill, New York, 1996, pp. 934-935
El-Hariri, L. M. et al., J. Pharm. Pharmacol., 1992, 44, pp. 651-654
Krieg, A. M, et al., Annu. Rev. Immunol., 2002, 20, pp. 709-760
Langer et al Science, 1990, 249, pp. 1527-1533

Lee et al., Critical Reviews in Therapeutic Drug Carrier Systems, 1991, pp. 92ff
Lefebure, C. et al., Eur. Cytokine Netw, 1995, 6, pp. 7-19
Lewis, D. H., et al Drug and Pharmaceutical Sciences, 1990
Muranishi, Critical Reviews in Therapeutic Drug Carrier Systems, 1990, 7, pp. 1-33
Nielsen P. E. et al, Science, 1991, 254 (5037), pp. 1497-1500
Schlingensiepen, R. et al, The Oligonucleotide, 2005, 15(2), pp. 94-104
Takahasi, H. et al., J. Pharm. Pharmacol., 1988, 40, pp. 252-257
Theodosopoulos et al., Proc. Am. Soc. Clin. Oncol., 2001, 20, pp. 2059 ff
Yamashita, S. et al., J. Pharm. Pharmacol., 1987, 39, pp. 621-626
Wagner, et al., Science, 1993, 260, pp. 1510-1513
Wang and Martini, Clin. Invest., 1996/97, pp. 448-454

The invention claimed is:

1. A method for treatment of glioma, which method comprises administering intratumorally to said glioma in a human subject, at a flow rate of 2 μl/min to 10 μl/min for 4 to 14 days, at least one oligonucleotide with a length of from 8 to 30 nucleotides, wherein said oligonucleotide hybridizes with a messenger RNA of a TGF-β2 and is contained in a composition that comprises said oligonucleotide in a concentration of 1 μM to 25 μM.

2. The method of claim 1, wherein the oligonucleotide is included in said composition in a concentration of 1 μM to 15 μM.

3. The method of claim 1, wherein at least one nucleotide in said oligonucleotide is a ribonucleotide that has a 2'-modification.

4. The method of claim 1, wherein said oligonucleotide is a single-stranded oligonucleotide.

5. The method of claim 1, wherein at least one linkage between two consecutive nucleotides in said oligonucleotide is a phosphorothioate or a methylphosphonate.

6. The method of claim 1, wherein said administering is for 3 to 8 days.

7. The method of claim 1, wherein said administering is in a plurality of courses.

8. The method of claim 3, wherein said 2' modification is methoxy or methoxyethyloxy.

9. The method of claim 7, wherein the administering is 2-20 times.

* * * * *

SEQUENCE LISTING

```
<160> NUMBER OF SEQ ID NOS: 91

<210> SEQ ID NO 1
<211> LENGTH: 14
<212> TYPE: DNA
<213> ORGANISM: homo sapiens

<400> SEQUENCE: 1
gtagtacacg atgg                                                         14

<210> SEQ ID NO 2
<211> LENGTH: 18
<212> TYPE: DNA
<213> ORGANISM: homo sapiens

<400> SEQUENCE: 2
ctgatgtgtt gaagaaca                                                     18

<210> SEQ ID NO 3
<211> LENGTH: 16
<212> TYPE: DNA
<213> ORGANISM: homo sapiens

<400> SEQUENCE: 3
ctctgatgtg ttgaag                                                       16

<210> SEQ ID NO 4
<211> LENGTH: 14
<212> TYPE: DNA
<213> ORGANISM: homo sapiens

<400> SEQUENCE: 4
cgatagtctt gcag                                                         14

<210> SEQ ID NO 5
<211> LENGTH: 18
<212> TYPE: DNA
<213> ORGANISM: homo sapiens

<400> SEQUENCE: 5
cggcatgtct attttgta                                                     18

<210> SEQ ID NO 6
<211> LENGTH: 20
<212> TYPE: DNA
<213> ORGANISM: homo sapiens

<400> SEQUENCE: 6
gctttcacca aattggaagc                                                   20

<210> SEQ ID NO 7
<211> LENGTH: 14
<212> TYPE: DNA
```

<213> ORGANISM: homo sapiens

<400> SEQUENCE: 7
ctggcttttg ggtt                                                    14

<210> SEQ ID NO 8
<211> LENGTH: 14
<212> TYPE: DNA
<213> ORGANISM: homo sapiens

<400> SEQUENCE: 8
cagcacacag tagt                                                    14

<210> SEQ ID NO 9
<211> LENGTH: 14
<212> TYPE: DNA
<213> ORGANISM: homo sapiens

<400> SEQUENCE: 9
tcgagcttcc ccca                                                    14

<210> SEQ ID NO 10
<211> LENGTH: 14
<212> TYPE: DNA
<213> ORGANISM: homo sapiens

<400> SEQUENCE: 10
ccccgagccc aagg                                                    14

<210> SEQ ID NO 11
<211> LENGTH: 13
<212> TYPE: DNA
<213> ORGANISM: homo sapiens

<400> SEQUENCE: 11
cccgacgagc cgg                                                     13

<210> SEQ ID NO 12
<211> LENGTH: 14
<212> TYPE: DNA
<213> ORGANISM: homo sapiens

<400> SEQUENCE: 12
acgcaccaag gcga                                                    14

<210> SEQ ID NO 13
<211> LENGTH: 15
<212> TYPE: DNA
<213> ORGANISM: homo sapiens

<400> SEQUENCE: 13 cggggttgtcg agccc                                                  15

<210> SEQ ID NO 14
<211> LENGTH: 13
<212> TYPE: DNA
<213> ORGANISM: homo sapiens

<400> SEQUENCE: 14
cggcagtgcc ccg                                                     13

<210> SEQ ID NO 15
<211> LENGTH: 14
<212> TYPE: DNA

```
<213> ORGANISM: homo sapiens

<400> SEQUENCE: 15
cgcaattctg ctcg                                                    14

<210> SEQ ID NO 16
<211> LENGTH: 14
<212> TYPE: DNA
<213> ORGANISM: homo sapiens

<400> SEQUENCE: 16
ttcgttgtgc tccc                                                    14

<210> SEQ ID NO 17
<211> LENGTH: 14
<212> TYPE: DNA
<213> ORGANISM: homo sapiens

<400> SEQUENCE: 17
attccgactc ggtg                                                    14

<210> SEQ ID NO 18
<211> LENGTH: 17
<212> TYPE: DNA
<213> ORGANISM: homo sapiens

<400> SEQUENCE: 18
acgtgcgtca tcaccgt                                                 17

<210> SEQ ID NO 19
<211> LENGTH: 10
<212> TYPE: DNA
<213> ORGANISM: homo sapiens

<400> SEQUENCE: 19
ccaagaagcc                                                         10

<210> SEQ ID NO 20
<211> LENGTH: 14
<212> TYPE: DNA
<213> ORGANISM: homo sapiens

<400> SEQUENCE: 20
cctaatgcct tcca                                                    14

<210> SEQ ID NO 21
<211> LENGTH: 14
<212> TYPE: DNA
<213> ORGANISM: homo sapiens

<400> SEQUENCE: 21
tcagcagggc cagg                                                    14

<210> SEQ ID NO 22
<211> LENGTH: 17
<212> TYPE: DNA
<213> ORGANISM: homo sapiens

<400> SEQUENCE: 22
gcaaagttca gcagggc                                                 17

<210> SEQ ID NO 23
<211> LENGTH: 16
<212> TYPE: DNA
```

<213> ORGANISM: homo sapiens

<400> SEQUENCE: 23
ggcaaagttc agcagg                                                    16

<210> SEQ ID NO 24
<211> LENGTH: 18
<212> TYPE: DNA
<213> ORGANISM: homo sapiens

<400> SEQUENCE: 24
gtggcaaagt tcagcagg                                                  18

<210> SEQ ID NO 25
<211> LENGTH: 14
<212> TYPE: DNA
<213> ORGANISM: homo sapiens

<400> SEQUENCE: 25
gtggcaaagt tcag                                                      14

<210> SEQ ID NO 26
<211> LENGTH: 18
<212> TYPE: DNA
<213> ORGANISM: homo sapiens

<400> SEQUENCE: 26
gaccgtggca aagttcag                                                  18

<210> SEQ ID NO 27
<211> LENGTH: 15
<212> TYPE: DNA
<213> ORGANISM: homo sapiens

<400> SEQUENCE: 27
agagaggctg accgt                                                     15

<210> SEQ ID NO 28
<211> LENGTH: 17
<212> TYPE: DNA
<213> ORGANISM: homo sapiens

<400> SEQUENCE: 28
gagagagaga ggctgac                                                   17

<210> SEQ ID NO 29
<211> LENGTH: 15
<212> TYPE: DNA
<213> ORGANISM: homo sapiens

<400> SEQUENCE: 29
acagagagag gctga                                                     15

<210> SEQ ID NO 30
<211> LENGTH: 15
<212> TYPE: DNA
<213> ORGANISM: homo sapiens

<400> SEQUENCE: 30
gtggacagag agagg                                                     15

<210> SEQ ID NO 31
<211> LENGTH: 18
<212> TYPE: DNA

<213> ORGANISM: homo sapiens

<400> SEQUENCE: 31
caactggaca gagagagg                                                 18

<210> SEQ ID NO 32
<211> LENGTH: 16
<212> TYPE: DNA
<213> ORGANISM: homo sapiens

<400> SEQUENCE: 32
tcttcttgat gtggcc                                                   16

<210> SEQ ID NO 33
<211> LENGTH: 17
<212> TYPE: DNA
<213> ORGANISM: homo sapiens

<400> SEQUENCE: 33
ccctcttctt cttgatg                                                  17

<210> SEQ ID NO 34
<211> LENGTH: 14
<212> TYPE: DNA
<213> ORGANISM: homo sapiens

<400> SEQUENCE: 34
caccctcttc ttct                                                     14

<210> SEQ ID NO 35
<211> LENGTH: 17
<212> TYPE: DNA
<213> ORGANISM: homo sapiens

<400> SEQUENCE: 35
atggatttct ttggcat                                                  17

<210> SEQ ID NO 36
<211> LENGTH: 13
<212> TYPE: DNA
<213> ORGANISM: homo sapiens

<400> SEQUENCE: 36
ggatttcttt ggc                                                      13

<210> SEQ ID NO 37
<211> LENGTH: 18
<212> TYPE: DNA
<213> ORGANISM: homo sapiens

<400> SEQUENCE: 37
aagttggact ctcttctc                                                 18

<210> SEQ ID NO 38
<211> LENGTH: 18
<212> TYPE: DNA
<213> ORGANISM: homo sapiens

<400> SEQUENCE: 38
taagttggac tctcttct                                                 18

<210> SEQ ID NO 39
<211> LENGTH: 16
<212> TYPE: DNA

<213> ORGANISM: homo sapiens

<400> SEQUENCE: 39
taggagtggt tgaggc                                                  16

<210> SEQ ID NO 40
<211> LENGTH: 17
<212> TYPE: DNA
<213> ORGANISM: homo sapiens

<400> SEQUENCE: 40
gtgtaggagt ggttgag                                                 17

<210> SEQ ID NO 41
<211> LENGTH: 14
<212> TYPE: DNA
<213> ORGANISM: homo sapiens

<400> SEQUENCE: 41
ctgtgtagga gtgg                                                    14

<210> SEQ ID NO 42
<211> LENGTH: 14
<212> TYPE: DNA
<213> ORGANISM: homo sapiens

<400> SEQUENCE: 42
cccacatgcc tgtg                                                    14

<210> SEQ ID NO 43
<211> LENGTH: 14
<212> TYPE: DNA
<213> ORGANISM: homo sapiens

<400> SEQUENCE: 43
cgatgaacaa cgag                                                    14

<210> SEQ ID NO 44
<211> LENGTH: 16
<212> TYPE: DNA
<213> ORGANISM: homo sapiens

<400> SEQUENCE: 44
ctggcgatga acaacg                                                  16

<210> SEQ ID NO 45
<211> LENGTH: 14
<212> TYPE: DNA
<213> ORGANISM: homo sapiens

<400> SEQUENCE: 45
cgctggcgat gaac                                                    14

<210> SEQ ID NO 46
<211> LENGTH: 15
<212> TYPE: DNA
<213> ORGANISM: homo sapiens

<400> SEQUENCE: 46
gagctagtcc cgttg                                                   15

<210> SEQ ID NO 47
<211> LENGTH: 15
<212> TYPE: DNA

<213> ORGANISM: homo sapiens

<400> SEQUENCE: 47
gcgaagagct agtcc                                                    15

<210> SEQ ID NO 48
<211> LENGTH: 17
<212> TYPE: DNA
<213> ORGANISM: homo sapiens

<400> SEQUENCE: 48
ccagttatgc gaagagc                                                  17

<210> SEQ ID NO 49
<211> LENGTH: 16
<212> TYPE: DNA
<213> ORGANISM: homo sapiens

<400> SEQUENCE: 49
ccccagttat gcgaag                                                   16

<210> SEQ ID NO 50
<211> LENGTH: 17
<212> TYPE: DNA
<213> ORGANISM: homo sapiens

<400> SEQUENCE: 50
cggctcaccg cctcggc                                                  17

<210> SEQ ID NO 51
<211> LENGTH: 18
<212> TYPE: DNA
<213> ORGANISM: homo sapiens

<400> SEQUENCE: 51
catttgttgt gctgtagg                                                 18

<210> SEQ ID NO 52
<211> LENGTH: 18
<212> TYPE: DNA
<213> ORGANISM: homo sapiens

<400> SEQUENCE: 52
ggtctgcatt cacatttg                                                 18

<210> SEQ ID NO 53
<211> LENGTH: 18
<212> TYPE: DNA
<213> ORGANISM: homo sapiens

<400> SEQUENCE: 53
catctgcaag tacgttcg                                                 18

<210> SEQ ID NO 54
<211> LENGTH: 18
<212> TYPE: DNA
<213> ORGANISM: homo sapiens

<400> SEQUENCE: 54
cacatctgca agtacgtt                                                 18

<210> SEQ ID NO 55
<211> LENGTH: 18
<212> TYPE: DNA

<213> ORGANISM: homo sapiens

<400> SEQUENCE: 55
gtcacatctg caagtacg                18

<210> SEQ ID NO 56
<211> LENGTH: 18
<212> TYPE: DNA
<213> ORGANISM: homo sapiens

<400> SEQUENCE: 56
gcttgaagat gtacctcg                18

<210> SEQ ID NO 57
<211> LENGTH: 18
<212> TYPE: DNA
<213> ORGANISM: homo sapiens

<400> SEQUENCE: 57
gtaaaactgg atcatctc                18

<210> SEQ ID NO 58
<211> LENGTH: 18
<212> TYPE: DNA
<213> ORGANISM: homo sapiens

<400> SEQUENCE: 58
cttcttttgc aagtctgt                18

<210> SEQ ID NO 59
<211> LENGTH: 18
<212> TYPE: DNA
<213> ORGANISM: homo sapiens

<400> SEQUENCE: 59
tgagctgtgc atgccttc                18

<210> SEQ ID NO 60
<211> LENGTH: 15
<212> TYPE: DNA
<213> ORGANISM: homo sapiens

<400> SEQUENCE: 60
agtcaggagg accag                15

<210> SEQ ID NO 61
<211> LENGTH: 15
<212> TYPE: DNA
<213> ORGANISM: homo sapiens

<400> SEQUENCE: 61
tgggtgccct ggcct                15

<210> SEQ ID NO 62
<211> LENGTH: 15
<212> TYPE: DNA
<213> ORGANISM: homo sapiens

<400> SEQUENCE: 62
catgttaggc aggtt                15

<210> SEQ ID NO 63
<211> LENGTH: 17
<212> TYPE: DNA

<213> ORGANISM: homo sapiens

<400> SEQUENCE: 63
aggcatctcg gagatct                                                17

<210> SEQ ID NO 64
<211> LENGTH: 16
<212> TYPE: DNA
<213> ORGANISM: homo sapiens

<400> SEQUENCE: 64
aaagtcttca ctctgc                                                 16

<210> SEQ ID NO 65
<211> LENGTH: 17
<212> TYPE: DNA
<213> ORGANISM: homo sapiens

<400> SEQUENCE: 65
aacaagttgt ccagctg                                                17

<210> SEQ ID NO 66
<211> LENGTH: 15
<212> TYPE: DNA
<213> ORGANISM: homo sapiens

<400> SEQUENCE: 66
catcacctcc tccag                                                  15

<210> SEQ ID NO 67
<211> LENGTH: 18
<212> TYPE: DNA
<213> ORGANISM: homo sapiens

<400> SEQUENCE: 67
gggtcttcag gttctccc                                               18

<210> SEQ ID NO 68
<211> LENGTH: 18
<212> TYPE: DNA
<213> ORGANISM: homo sapiens

<400> SEQUENCE: 68
cacggccttg ctcttgtt                                               18

<210> SEQ ID NO 69
<211> LENGTH: 18
<212> TYPE: DNA
<213> ORGANISM: homo sapiens

<400> SEQUENCE: 69
ttattaaagg cattcttc                                               18

<210> SEQ ID NO 70
<211> LENGTH: 18
<212> TYPE: DNA
<213> ORGANISM: homo sapiens

<400> SEQUENCE: 70
aagatgtcaa actcactc                                               18

<210> SEQ ID NO 71
<211> LENGTH: 18
<212> TYPE: DNA

<213> ORGANISM: homo sapiens

<400> SEQUENCE: 71
gtagttgatg aagatgtc					18

<210> SEQ ID NO 72
<211> LENGTH: 16
<212> TYPE: DNA
<213> ORGANISM: homo sapiens

<400> SEQUENCE: 72
gattttggag acctct					16

<210> SEQ ID NO 73
<211> LENGTH: 16
<212> TYPE: DNA
<213> ORGANISM: homo sapiens

<400> SEQUENCE: 73
tcagctatcc cagagc					16

<210> SEQ ID NO 74
<211> LENGTH: 15
<212> TYPE: DNA
<213> ORGANISM: homo sapiens

<400> SEQUENCE: 74
ggctgggtca gctat					15

<210> SEQ ID NO 75
<211> LENGTH: 18
<212> TYPE: DNA
<213> ORGANISM: homo sapiens

<400> SEQUENCE: 75
aaatcgttca cagagaag					18

<210> SEQ ID NO 76
<211> LENGTH: 18
<212> TYPE: DNA
<213> ORGANISM: homo sapiens

<400> SEQUENCE: 76
tctttctaaa tcgttcac					18

<210> SEQ ID NO 77
<211> LENGTH: 16
<212> TYPE: DNA
<213> ORGANISM: homo sapiens

<400> SEQUENCE: 77
cagttcggac tatact					16

<210> SEQ ID NO 78
<211> LENGTH: 14
<212> TYPE: DNA
<213> ORGANISM: homo sapiens

<400> SEQUENCE: 78
gcccaagttc aaca						14

<210> SEQ ID NO 79
<211> LENGTH: 16
<212> TYPE: DNA

```
<213> ORGANISM: homo sapiens

<400> SEQUENCE: 79
catagaaggt cgtttc                                                    16

<210> SEQ ID NO 80
<211> LENGTH: 14
<212> TYPE: DNA
<213> ORGANISM: homo sapiens

<400> SEQUENCE: 80
aggtttgcgt agac                                                      14

<210> SEQ ID NO 81
<211> LENGTH: 16
<212> TYPE: DNA
<213> ORGANISM: homo sapiens

<400> SEQUENCE: 81
gttcctcatg cgcttc                                                    16

<210> SEQ ID NO 82
<211> LENGTH: 14
<212> TYPE: DNA
<213> ORGANISM: homo sapiens

<400> SEQUENCE: 82
gtttgcaact gctg                                                      14

<210> SEQ ID NO 83
<211> LENGTH: 18
<212> TYPE: DNA
<213> ORGANISM: homo sapiens

<400> SEQUENCE: 83
gtccgtgcag aagtcctg                                                  18

<210> SEQ ID NO 84
<211> LENGTH: 18
<212> TYPE: DNA
<213> ORGANISM: homo sapiens

<400> SEQUENCE: 84
ggaagaaact atgagagt                                                  18

<210> SEQ ID NO 85
<211> LENGTH: 18
<212> TYPE: DNA
<213> ORGANISM: homo sapiens

<400> SEQUENCE: 85
cttagggaag aaactatg                                                  18

<210> SEQ ID NO 86
<211> LENGTH: 16
<212> TYPE: DNA
<213> ORGANISM: homo sapiens

<400> SEQUENCE: 86
agaacaaaga agagcc                                                    16

<210> SEQ ID NO 87
<211> LENGTH: 16
<212> TYPE: DNA
```

```
<213> ORGANISM: homo sapiens

<400> SEQUENCE: 87
cagcaagaga acaaag                                                   16

<210> SEQ ID NO 88
<211> LENGTH: 18
<212> TYPE: DNA
<213> ORGANISM: homo sapiens

<400> SEQUENCE: 88
cgacattcag taaaagtg                                                 18

<210> SEQ ID NO 89
<211> LENGTH: 18
<212> TYPE: DNA
<213> ORGANISM: homo sapiens

<400> SEQUENCE: 89
cttctggaga taactaga                                                 18

<210> SEQ ID NO 90
<211> LENGTH: 18
<212> TYPE: DNA
<213> ORGANISM: homo sapiens

<400> SEQUENCE: 90
cataagacac agtcttac                                                 18

<210> SEQ ID NO 91
<211> LENGTH: 18
<212> TYPE: DNA
<213> ORGANISM: Homo sapiens

<400> SEQUENCE: 91
gaaagcataa gacacagt                                                 18
```